US008237015B2

(12) United States Patent  (10) Patent No.: US 8,237,015 B2
Luo  (45) Date of Patent: Aug. 7, 2012

(54) METHODS AND COMPOSITIONS FOR AN INTEGRATED DUAL SITE-SPECIFIC RECOMBINATION SYSTEM FOR PRODUCING ENVIRONMENTALLY SAFE AND CLEAN TRANSGENIC PLANTS

(75) Inventor: Hong Luo, Clemson, SC (US)

(73) Assignee: Clemson University Research Foundation, Clemson, SC (US)

( * ) Notice: Subject to any disclaimer, the term of this patent is extended or adjusted under 35 U.S.C. 154(b) by 1004 days.

(21) Appl. No.: 12/174,066

(22) Filed: Jul. 16, 2008

(65) Prior Publication Data

US 2009/0025104 A1    Jan. 22, 2009

Related U.S. Application Data

(60) Provisional application No. 60/950,049, filed on Jul. 16, 2007.

(51) Int. Cl.
 *C12N 15/82* (2006.01)
 *A01H 5/00* (2006.01)
 *A01H 5/10* (2006.01)
(52) U.S. Cl. ........ 800/278; 800/300; 800/260; 800/288; 435/320.1
(58) Field of Classification Search .................. 800/287, 800/278, 279; 435/468
See application file for complete search history.

(56) References Cited

U.S. PATENT DOCUMENTS

| | | | |
|---|---|---|---|
| 6,110,736 A * | 8/2000 | Hodges et al. ............. | 435/320.1 |
| 7,238,854 B2 | 7/2007 | Yadav et al. | |
| 2002/0023278 A1* | 2/2002 | Lyznik et al. ................. | 800/278 |
| 2003/0110532 A1* | 6/2003 | Armostrong et al. ......... | 800/279 |
| 2003/0188341 A1* | 10/2003 | Luo et al. ...................... | 800/286 |
| 2003/0194809 A1* | 10/2003 | Yadav et al. ................... | 435/468 |
| 2004/0185567 A1* | 9/2004 | Rouwendal .................... | 435/468 |
| 2005/0235379 A1* | 10/2005 | Luo et al. ...................... | 800/287 |

OTHER PUBLICATIONS

International Search Report and Written Opinion for International Application No. PCT/US08/08672; mailed Dec. 24, 2008 (13 pages).
Ainley and Key. "Development of a Heat Shock Inducible Expression Cassette for Plants: Characterization of Parameters for its Use in Transient Expression Assays" *Plant Molecular Biology* 14:949-967 (1990).
Argos et al. "The Integrase Family of Site-Specific Recombinases: Regional Similarities and Global Diversity" *The EMBO Journal* 5(2):433-440 (1986).
Austin et al. "A Novel Role for Site-Specific Recombination in Maintenance of Bacterial Replicons" *Cell* 25:729-736 (1981).
Bar et al. "Visual Characterization of Recombination of FRT-*gusA* Loci in Transgenic Tobacco Mediated by Constitutive Expression of the Native FLP Recombinase" *Theor Appl Genet* 93:407-413 (1996).
Bayley et al. "Exchange of Gene Activity in Transgenic Plants Catalyzed by the Cre-*lox* Site-Specific Recombination System" *Plant Molecular Biology* 18:353-361 (1992).
Broach et al. "Recombination Within the Yeast Plasmid 2μCircle is Site-Specific" *Cell* 29:227-234 (1982).
Coen et al. "*floricaula*: A Homeotic Gene Required for Flower Development in *Antirrhinum majus*" *Cell* 63:1311-1322 (1990).
Craig. "The Mechanism of Conservative Site-Specific Recombination" *Annu Rev Genet* 22:77-105 (1988).
Cueller et al. "Self-Excision of the Antibiotic Resistance Gene *nptII* Using a Heat Inducible *Cre-loxP* System From Transgenic Potato" *Plant Mol Biol* 62:71-82 (2006).
Dale and Ow. "Intra- and Intermolecular Site-Specific Recombination in Plant Cells Mediated by Bacteriophage P1 Recombinase" *Gene* 91:79-85 (1990).
Dale and Ow. "Gene Transfer With Subsequent Removal of the Selection Gene from the Host Genome" *Proc. Natl. Acad. Sci. USA* 88:10558-10562 (1991).
Daniell. "Molecular Strategies for Gene Containment in Transgenic Crops" *Nature Biotechnology* 20:581-586 (2002).
DeBlock et al., "Engineering Herbicide Resistance in Plants by Expression of a Detoxifying Enzyme" *The EMBO Journal* 6(9):2513-2518 (1987).
DeBlock et al. "Expression of Foreign Genes in Regenerated Plants and in Their Progeny" *The EMBO Journal* 3(8):1681-1689 (1984).
DeBlock et al. "The Development of a Nuclear Male Sterility System in Wheat. Expression of the *barnase* Gene Under the Control of Tapetum Specific Promoters" *Theor Appl Genet* 95:125-131 (1997).
DeBlock et al. "Transformation of *Brassica napus* and *Brassica oleracea* Using *Agrobacterium tumefaciens* and the Expression of the *bar* and *neo* Genes in the Transgenic Plants" *Plant Physiol* 91:694-701 (1989).
Fei and Nelson. "Greenhouse Evaluation of Fitness-Related Reproductive Traits in Roundup®-Tolerant Transgenic Creeping Bentgrass (*Agrostis stolonifera* I.)" *In Vitro Cell Dev Biol—Plant* 40:266-273 (2004).
Fraley et al. "Expression of Bacterial Genes in Plant Cells" *Proc Natl Acad Sci USA* 80:4803-4807 (1983).
Gardner and Danneberger. "Relative Fitness of Glyphosate-Resistant Creeping Bentgrass Lines in Kentucky Bluegrass" *HortScience* 38(3):455-459 (2003).
Gardner et al. "Lateral Spread of Glyphosate-Resistant Transgenic Creeping Bentgrass (*Agrostis stolonifera*) Lines in Established Turfgrass Swards" *Weed Technology* 18:773-778 (2004).
Goetz et al. "Induction of Male Sterility in Plants by Metabolic Engineering of the Carbohydrate Supply" *Proc Natl Acad Sci USA* 98(11):6522-6527 (2001).
Golic and Lindquist. "The FLP Recombinase of Yeast Catalyzes Site-Specific Recombination in the *Drosophila* Genome" *Cell* 59:499-509 (1989).

(Continued)

*Primary Examiner* — Anne Kubelik

(74) *Attorney, Agent, or Firm* — Myers Bigel Sibley & Sajovec, PA

(57) ABSTRACT

The present invention is directed to the use of multiple site-specific recombination systems for use in transgene containment in plants. More specifically, the present invention describes coordinated excisional DNA recombination by multiple (e.g., dual) recombinases to achieve excision of unwanted transgenic DNA as well as recombinase-coding sequences themselves by self-excision. Further, the simultaneous use of multiple site-specific recombination systems in combination with controllable total sterility technology (i.e., no or reduced sexual reproduction), provides the production of environmentally safe, clean transgenic plants, enhancing the capability and public acceptance of transgenic technology for plant trait modification.

39 Claims, 4 Drawing Sheets

OTHER PUBLICATIONS

Gordon-Kamm et al. "Transformation of Maize Cells and Regeneration of Fertile Transgenic Plants" *The Plant Cell* 2:603-618 (1990).
Hoa et al. "*Cre-lox* Site-Specific Recombination Controls the Excision of a Transgene from the Rice Genome" *Thero Appl Genet* 104:518-525 (2002).
Hoess et al. "P1 Site-Specific Recombination: Nucleotide Sequence of the Recombining Sites" *Proc Natl Acad Sci USA* 79:3398-3402 (1982).
Hu et al. "FLP-Mediated Site-Specific Recombination for Genome Modification in Turfgrass" *Biotechnol Lett* 28:1793-1804 (2006).
Hu et al. "FLP Recombinase-Mediated Site-Specific Recombination in Rice" *Plant Biotechnology Journal* 6:176-188 (2008).
Jagannath et al. "The Use of a Spacer DNA Fragment Insulates the Tissue-Specific Expression of a Cytotoxic Gene (*barnase*) and Allows High-Frequency Generation of Transgenic Male Sterile Lines in *Brassica juncea* L." *Molecular Breeding* 8:11-23 (2001).
Jayaram. "Two-Micrometer Circle Site-Specific Recombination: The Minimal Substrate and the Possible Role of Flanking Sequences" *Proc Natl Acad Sci USA* 82:5875-5879 (1985).
Jefferson. "Assaying Chimeric Genes in Plants: The GUS Gene Fusion System" *Plant Molecular Biology Reporter* 5(4):387-405 (1987).
Kilby et al. "FLP Recombinase in Transgenic Plants: Constitutive Activity in Stably Transformed Tobacco and Generation of Marked Cell Clones in *Arabidopsis*" *The Plant Journal* 8(5):637-652 (1995).
Koncz et al. "Expression and Assembly of Functional Bacterial Luciferase in Plants" *Proc Natl Aced Sci USA* 84:131-135 (1987).
Lloyd and Davis. "Functional Expression of the Yeast FLP/FRT Site-Specific Recombination System in *Nicotiana tabacum*" *Mol Gene Genet* 242:653-657 (1994).
Luo and Kausch. "Application of FLP/FRT Site-Specific DNA Recombination System in Plants" In: *Genetic Engineering, Principles and Methods*, vol. 24 (Jane K. Setlow, ed.), Kluwer Academic/Pleum Publishers, New York, NY, pp. 1-16 (2002).
Luo et al. "*Agrobacterium tumefacines*-Mediated Creeping Bentgrass (*Agrostis stolonifera* L.) Transformation Using Phospinothricin Selection Results in a High Frequency of Single-Copy Transgene Integration" *Plant Cell Rep* 22:645-652 (2004).
Luo et al. "Controlling Transgene Escape in GM Creeping Bentgrass" *Molecular Breeding* 16:185-188 (2005).
Luo et al. "Controlling Transgene Escape in Genetically Modified Grasses" In: *Molecular Breeding of Forage and Turf*, (Hopkins A., Wang Z.Y., Mian R., Sledge M. and Barker R., eds.), Kluwer Academic Publishers, Dordrecht/Boston/London, pp. 245-254 (2004).
Luo et al. "FLP-Mediated Recombination for Use in Hybrid Plant Production" *The Plant Journal* 23(3):423-430 (2000).
Luo et al. "*RTS*, a Rice Anther-Specific Gene is Required for Male Fertility and its Promoter Sequence Directs Tissue-Specific Gene Expression in Different Plant Species" *Plant Mol Biol* 62:397-408 (2006).
Lyznik et al. "Activity of Yeast FLP Recombinase in Maize and Rice Protoplasts" *Nucleic Acids Research* 21(4):969-975 (1993).
Lyznik et al. "FLP-Mediated Recombination of *FRT* Sites in the Maize Genome" *Nucleic Acids Research* 24(19):3784-3789 (1996).
Lyznik et al. "Heat-Inducible Expression of *FLP* Gene in Maize Cells" *The Plant Journal* 8(2):177-186 (1995).
Mariani et al. "Induction of Male Sterility in Plants by a Chimaeric Ribonuclease Gene" *Nature* 347:737-741 (1990).
Moffatt and Somerville. "Positive Selection for Male-Sterile Mutants of *Arabidopsis* Lacking Adenine Phosphoribosyl Transferase Activity" *Plant Physiol* 86:1150-1154 (1988).
Odell et al. "Site-Directed Recombination in the Genome of Transgenic Tobacco" *Mol Gen Genet* 223:369-378 (1990).
Odell and Russell. "Use of Site-Specific Recombination Systems in Plants" In: *Homologous Recombination in Plants*, (J. Paszkowski, ed.), J. Dordrecht: Kluwer Academic Publishers, pp. 219-270 (1994).
O'Gorman et al. "Recombinase-Mediated Gene Activation and Site-Specific Integration in Mammalian Cells" *Science* 251:1351-1355 (1991).
Osborne et al. "A System for Insertional Mutagenesis and Chromosomal Rearrangement Using the Ds Transposon and Cre-*lox*" *The Plant Journal* 7(4):687-701 (1995).

Ow and Medberry. "Genome Manipulation Through Site-Specific Recombination" *Critical Reviews in Plant Sciences* 14(3):239-261 (1995).
Padidam. "Chemically Regulated Gene Expression in Plants" *Current Opinion in Plant Biology* 6:169-177 (2003).
Qin et al. "Cre Recombinase-Mediated Site-Specific Recombination Between Plant Chromosomes" *Proc Nati Acad Sci USA* 91:1706-1710 (1994).
Rieping and Schöffl. "Synergistic Effect of Upstream Sequences, CCAAT Box Elements, and HSE Sequences for Enhanced Expression of Chimaeric Heat Shock Genes in Transgenic Tobacco" *Mol Gen Genet* 231:226-232 (1992).
Roslan et al. "Characterization of the Ethanol-Inducible *alc* Gene-Expression System in *Arabidopsis thaliana*" *The Plant Journal* 28(2):225-235 (2001).
Russell et al. "Directed Excision of a Transgene from the Plant Genome" *Mol Gene Genet* 234:49-59 (1992).
Samach et al. "Distinct Roles of Constans Target Genes in Reproductive Development of *Arabidopsis*" *Science* 288:1613-1616 (2000).
Shimizu-Sato et al. "A Light-Switchable Gene Promoter System" *Nature Biotechnology* 20:1041-1044 (2002).
Simpson and Dean. "*Arabidopsis*, the Rosetta Stone of Flowering Time?" *Science* 296:285-289 (2002).
Sonti et al. "Activity of the Yeast FLP Recombinase in *Arabidopsis*" *Plant Molecular Biology* 28:1127-1132 (1995).
Spena et al. "Construction of a Heat-Inducible Gene for Plants. Demonstration of Heat-Inducible Activity of the *Drosophila* hsp70 Promoter in Plants" *The EMBO Journal* 4(11):2739-2743 (1985).
Sreekala et al. "Excision of a Selectable Marker in Transgenic Rice (*Oryza sativa* L.) Using a Chemically Regulated CRE/*loxP* System" *Plant Cell Rep* 24:86-94 (2005).
Srivastava et al. "Single-Copy Transgenic Wheat Generated Through the Resolution of Comlex Integration Patterns" *Proc Natl Acad Sci USA* 96:11117-11121 (1999).
Srivastava et al. "Biolistic Mediated Site-Specific Integration in Rice" *Molecular Breeding* 8:345-350 (2001).
Stuurman et al. "Single-Site Manipulation of Tomato Chromosomes in vitro and in vivo Using Cre-*lox* Site-Specific Recombination" *Plant Molecular Biology* 32:901-913 (1996).
Toriyama et al. "Visualization of Somatic Deletions Mediated by R/*RS* Site-Specific Recombination and Induction of Germinal Deletions Caused by Callus Differentiation and Regeneration in Rice" *Plant Cell Rep* 21:605-610 (2003).
Tsuchiya et al. "Tapetum-Specific Expression of the Gene for an Endo-β-1,3-Glucanase Causes Male Sterility in Transgenic Tobacco" *Plant Cell Physiol* 36(3):487-494 (1995).
Van Den Elzen et al. "A Chimaeric Hygromycin Resistance Gene as a Selectable Marker in Plants" *Plant Molecular Biology* 5:299-302 (1985).
Wang et al. "Inducible Excision of Selectable Marker Gene from Transgenic Plants by the Cre/*lox* Site-Specific Recombination System" *Transgenic Research* 14:605-614 (2005).
Watrud et al. "Evidence for Landscape-Level, Pollen-Mediated Gene Flow from Genetically Modified Creeping Bentgrass with *CP4 EPSPS* as a Marker" *Proc Natl Acad Sci USA* 101(40)14533-14538 (2004).
Weigel et al. "LEAFY Controls Floral Meristem Identity in *Arabidopsis*" *Cell* 69:843-859 (1992).
Xu et al. "*Bcp1*, a Gene Required for Male Fertility in *Arabidopsis*" *Proc Natl Acad Sci USA* 92:2106-2110 (1995).
Zhang et al. "Chemical-Induced Autoexcision of Selectable Makers in Elite Tomato Plants Transformed with a Gene Conferring Resistance to Lepidopteran Insects" *Biotechnol Lett* 28:1247-1253 (2006).
Zik and Irish. "Flower Development: Initiation, Differentiation, and Diversification" *Annu Rev Cell Dev Biol* 19:119-140 (2003).
Zuo et al. "An Estrogen Receptor-Based Transactivator XVE Mediates Highly Inducible Gene Expression in Transgenic Plants" *The Plant Journal* 24(2):265-273 (2000).
Zuo et al. "Chemical-Regulated, Site-Specific DNA Excision in Transgenic Plants" *Nature Biotechnology* 19:157-161 (2001).

\* cited by examiner

METHODS AND COMPOSITIONS FOR AN INTEGRATED DUAL SITE-SPECIFIC RECOMBINATION SYSTEM FOR PRODUCING ENVIRONMENTALLY SAFE AND CLEAN TRANSGENIC PLANTS

STATEMENT OF PRIORITY

This application claims the benefit, under 35 U.S.C. §119(e), of U.S. Provisional Application No. 60/950,049, filed Jul. 16, 2007, the entire contents of which are incorporated by reference herein.

FIELD OF THE INVENTION

The present invention relates to methods and compositions for producing transgenic plants.

BACKGROUND OF THE INVENTION

Beneficial traits such as herbicide resistance, drought and stress tolerance, insect and pest resistance, phyto-remediation of soil contaminants, and horticultural qualities such as aluminum tolerance, stay-green appearance, pigmentation and growth habit are among a long list of features that can be improved in plants, including turfgrass, using transgene technology. However, the possibility of transgene escape from transgenic plants to wild and non-transformed species raises valid ecological concerns regarding commercialization of transgenic plants.

Although numerous risk assessment studies have been conducted on transgenic plants of annual and/or self-pollinating crops (Ellstrand and Hoffman, 1990; Hoffman, 1990; Dale, 1992; 1993; Rogers and Parkes, 1995; Ellstrand et al., 1999; Altieri, 2000; Dale et al., 2002; Eastham and Sweet, 2002; Stewart et al., 2003; Pilson and Prendeville, 2004; Marvier and Van Acker, 2005), very little information is available on the potential risks from the commercialization and large-scale seed production of perennial transgenic grasses.

In a three-year field study on gene flow of transgenic bentgrass, it was observed that pollen from the transgenic nursery traveled at least 978 feet (Wipff and Friker, 2000; 2001). A recent landscape-level study on pollen-mediated gene flow from genetically modified creeping bentgrass demonstrated long-distance viable pollen movement from multiple source fields of genetically modified creeping bentgrass (Watrud et al., 2004). A subsequent study by the same group documented establishment and distribution of transgenic plants in wild populations (Reichman et al., 2006). Spatial distribution and parentage of transgenic plants (as confirmed by analyses of nuclear ITS and chloroplast matK gene trees) suggested that establishment had resulted from both pollen-mediated intraspecific hybridizations and from crop seed dispersal. These results demonstrate that transgene flow from short-term production can result in establishment of transgenic plants at multi-kilometer distances from genetically modified source fields or plants (Reichman et al., 2006). Therefore, there is a need to develop methods that decrease, or even prevent transgene escape in a production field of transgenic plants before large-scale commercialization of such transgenic plants, including turfgrass.

In flowering plants, gene flow can occur through movement of pollen grains and seeds, with pollen flow often contributing the major component. With the availability of current molecular technologies, various gene containment strategies have been developed to alter gene flow by interfering with flower pollination, fertilization, and/or fruit development (Daniell, 2002). If transgenic plants can also be engineered as male sterile, there will be no viable pollen grains produced from the transgenic plants, thus preventing the potential risk of transgene escape into the surrounding environment by out-crossing with non-transgenic plants or wild species.

Site-specific recombination is a process involving reciprocal exchange between specific nucleic acid sites (referred to as target sites) catalyzed by specialized proteins known as site-specific recombinases (Craig, 1988). These recombinases can alter genomic DNA sequences in specific ways, providing powerful tools for the development of a new generation of molecular technology for crop improvement. Site-specific recombinases recognize specific DNA sequences, and in the presence of specific recombination sites they catalyze the recombination of DNA strands (Ow and Medberry, 1995). In these site-specific recombination systems, recombinases can catalyze excision or inversion of a DNA fragment according to the orientation of their specific target sites. Recombination between directly oriented sites leads to excision of the DNA between them, whereas recombination between inverted target sites causes inversion of the DNA between them The lambda integrase family of site-specific recombination systems consists of more than 100 different members. Among the most prominent of these are lambda Int, Cre/lox, FLP/FRT, R/RS, and Gin/gix. Recombinases such as Cre, FLP, R and Gin catalyze DNA recombination between their respective DNA substrates or target sites, loxP, FRT, RS and gix. These recombination systems use a common reaction pathway to carry out very different biological functions. They utilize a single polypeptide recombinase capable of recognizing a small DNA sequence without requiring any accessory factors. Cre/lox, FLP/FRT, R/RS, Gin/gix and λ-Int are probably the most utilized systems for genetic manipulation of plants and animals. In heterologous systems, Cre/lox, FLP/FRT, R/RS, Gin/gix carry out a freely reversible reaction, whereas λ-Int requires additional factors to carry out the reverse reaction. The minimal length of a loxP and FRT site is 34 bp (Hoess et al., 1982; Jayaram, 1985), and both of these consist of two 13-bp inverted repeats surrounding an 8-bp spacer region (boxed, see below), which confers directionality.

FLP (SEQ ID NO:1)

5'-GAAGTTCCTATAC TTTCTAGA GAATAGGAACTTC-3' loxP (SEQ ID NO:2)

5'-ATAACTTCGTATA ATGTATGC TATACGAAGTTAT-3'

In plants, the application of two site-specific recombination systems, the FLP/FRT system from the 2 µm plasmid of the eukaryote yeast (Broach et al., 1982) and the Cre/lox system from prokaryotic bacteriophage P1 (Austin et al., 1981), have been studied most extensively (Odell and Russell, 1994; Ow and Medberry, 1995; Luo and Kausch, 2002). The primary natural function of the Cre/lox and FLP/FRT systems is related to the amplification of extrachromosomal DNA molecules (bacteriophage or plasmid) in bacteria and yeast cells, respectively (Austin et al., 1981; Sadowski, 1995). Unlike another member of the integrase family of the site-specific recombinases, bacteriophage λ integrase (Argos et al., 1986), Cre and FLP recombinases do not require additional factors for controlling site-specific recombination reactions (Cox, 1983; Huang et al., 1991), making them good candidates for applications in heterologous organisms. The basic features of the FLP/FRT and the Cre/lox systems are that recombinases can catalyze the inversion, excision, and/or integration of nucleic acid fragments.

The Cre/lox recombination system from bacteriophage P1 was the first system evaluated in plant cells for its functionality in site-specific DNA recombination. In 1990, Dale and Ow demonstrated that Cre recombinase could excise, invert, or integrate extrachromosomal DNA molecules in tobacco protoplasts. In the same year, Odell et al. (1990) provided other crucial evidence that the Cre gene could be stably expressed in plant cells (tobacco), and that the Cre protein could recognize and recombine lox sites integrated into the plant genomic DNA. Further, the Cre gene has been shown to be successfully passed from one plant to another through cross-pollination The FLP/FRT recombination system, which functions endogenously in eukaryotic yeast cells, was also identified as having the capability of catalyzing efficient recombination reactions in heterologous eukaryotic cells (Golic and Lindquist, 1989; O'Gorman et al., 1991). Lyznik et al. (1993) used a modified FLP coding sequence from pOG44 (O'Gorman et al., 1991) to synthesize a chimeric plant FLP gene driven by the maize ubiquitin promoter to show activity of FLP recombinase in maize and rice cells. In 1994, Lloyd and Davis published a report on FLP-mediated activation of a hygromycin resistance gene in the tobacco genome by cross-pollination. Soon after, Lyznik et al. (1995; 1996) demonstrated that the activity of FLP/FRT system could be controlled in a precise manner in maize cells with high molecular fidelity.

Thus, both FLP/FRT and Cre/lox site-specific recombination systems have been shown, for example, to function not only in bacteria, yeast, insect cells, mammalian cells (Cox, 1983; Golic and Lindquist, 1989; Huang et al., 1991; O'Gonnan et al., 1991; Chou and Perrimon, 1992; Rong and Golic, 2000), but also in tobacco (Lloyd and Davis, 1994; Qin et al.1994; Bar et al., 1996), *Arabidopsis* (Odell et al., 1990; Dale and Ow, 1991; Bayley et al., 1992; Russel et al., 1992; Kilby et al., 1995; Osborne et al., 1995; Sonti et al., 1995; Luo et al., 2000), turfgrass (Luo et al., 2002; Hu et al., 2006), tomato (Stuurman et al., 1996; Zhang et al., 2006), maize and rice (Lyznik et al., 1993; 1995; 1996; Srivastava and Ow, 2001; Hoa et al., 2002; Toriyama et al., 2003; Sreekala et al., 2005), potato (Cuellar et al., 2006) and wheat (Srivastava et al., 1999).

Accordingly, in order to advance transgenic technologies for plant genetic improvement without the undesirable effects of gene flow, it would be useful to have a system in which a transgenic plant can be produced which has reduced or no sexual reproductive capability and further, in which unwanted transgenic nucleotide sequences are no longer present in the transgenic plant. Thus, the present invention provides methods and compositions wherein a dual recombination system is employed to achieve controlled excision of unwanted transgenic DNA and self excision of recombinase-coding genes in plants, thereby improving applications of plant transgenic technologies.

SUMMARY OF THE INVENTION

The present invention is directed to the use of multiple site-specific recombination systems for use in transgene containment in plants. More specifically, the present invention describes coordinated excisional DNA recombination by multiple (e.g., dual) recombinases to achieve excision of unwanted transgenic DNA as well as recombinase-coding sequences themselves by self-excision. Further, the simultaneous use of multiple site-specific recombination systems in combination with controllable total sterility technology (i.e., no or reduced sexual reproduction), provides the production of environmentally safe, clean transgenic plants, enhancing the capability and public acceptance of transgenic technology for plant trait modification.

Thus, a first aspect of the present invention is a method of producing a transgenic hybrid plant having no or reduced sexual reproduction, comprising: (a) stably transforming a first plant with a first nucleic acid construct comprising: (i) a promoter, P1; (ii) a site specific recombinase, RS1; (iii) a promoter, P2; (iv) a selectable marker, SM1; (v) a promoter P3; (vi) at least one nucleotide sequence the expression of which results in no or reduced sexual reproduction, NRSR; and (vii) at least two target sites, TRS2, specific for a site specific recombinase, RS2, that is different from the site specific recombinase, RS1, and further wherein P1 is operably located upstream of RS1, P2 is operably located upstream of SM1, P3 is operably located upstream of NRSR, a first TRS2 is located immediately downstream of P1 and a second TRS2 is located upstream of NRSR; (b) stably transforming a second plant with a second nucleic acid construct comprising: (i) a promoter, P4; (ii) a site specific recombinase, RS2, that is different from the site specific recombinase, RS1, of (a); (iii) a selectable marker, SM2; (iv) at least one nucleotide sequence of interest, NOI; (v) at least two target sites, TRS1, specific for the site specific recombinase, RS1; and (vi) at least two target sites, TRS2, specific for the site specific recombinase, RS2, and further wherein P4 is operably located upstream of SM2, RS2 is located downstream of SM2, a first TRS1 is located immediately downstream of P4, a second TRS1 is located immediately downstream of SM2, a first TRS2 is located immediately upstream of RS2 and downstream of the second TRS1, a second TRS2 is located immediately downstream of RS2 and the NOI is located immediately downstream of the second TRS2; and (c) cross-pollinating the stably transformed first plant of (a) with the stably transformed second plant of (b) to produce a transgenic hybrid plant having no or reduced sexual reproduction.

A further aspect of the present invention is a transgenic hybrid plant comprising: (a) a first nucleic acid construct comprising: (i) a promoter, P1; (ii) a target site, TRS2, specific for a site specific recombinase, RS2; and (iii) at least one nucleotide sequence the expression of which results in no or reduced sexual reproduction, NRSR, and wherein P1 is upstream of and operably associated with NRSR, and the target site, TRS2, is immediately downstream of P1; and (b) a second nucleic acid construct comprising: (i) a promoter, P4; (ii) a target site, TRS2, specific for the site specific recombinase of (a) (ii); (iii) a target site, TRS1, specific for a site specific recombinase, RS1; and (iv) at least one nucleotide sequence of interest, NOI, and wherein P4 is upstream of and operably associated with the NOI, and the target site, TRS1, is immediately downstream of P4 and the NOI is immediately downstream of TRS2.

An additional aspect of the invention is a method of reducing transgene flow to non-transgenic plants comprising, planting a field with a plurality of plants comprising a transgenic hybrid plant of the present invention.

The present invention also provides a nucleic acid construct comprising: (a) a promoter, P1; (b) a site specific recombinase, RS1; (c) a promoter, P2; (d) a selectable marker, SM1; (e) a promoter P3; (f) at least one nucleotide sequence the expression of which results in no or reduced sexual reproduction, NRSR; and (g) at least two target sites, TRS2, specific for a site specific recombinase, RS2, wherein RS2 is different from the site specific recombinase, RS1, of (b) above, and further wherein P1 is located upstream of and operably associated with RS1, P2 is located upstream of and operably associated with SM1, P3 is located upstream of and operably associated with NRSR, a first TRS2 is located immediately downstream of P1 and a second TRS2 is located upstream of NRSR.

Additionally provided is a nucleic acid construct comprising: (a) a promoter, P4; (b) a selectable marker, SM2; (c) a site specific recombinase, RS2; (d) at least two target sites, TRS2, specific for the site specific recombinase, RS2; (e) at least two target sites, TRS1, specific for a site specific recombinase, RS1, that is different from the site specific recombinase, RS2, of (c) above; and (f) at least one nucleotide sequence of interest, NOT; and further wherein P4 is located upstream of and operably associated with SM2, RS2 is located downstream of SM2, a first TRS1 is located immediately downstream of P4, a second TRS1 is located immediately downstream of SM2, a first TRS2 is located immediately upstream of RS2 and downstream of the second TRS1, a second TRS2 is located immediately downstream of RS2 and the NOT is located immediately downstream of the second TRS2.

A further embodiment of the present invention is a cell comprising a heterologous nucleic acid construct of this invention and a transgenic plant comprising a heterologous nucleic acid construct of the present invention.

An additional embodiment is a transgenic pollen grain of a transgenic plant of the present invention.

Also provided is a transgenic ovule of a transgenic plant of the present invention.

Additionally provided is a tissue culture of regenerable transgenic cells of a transgenic plant of the present invention.

Further provided is a seed of a transgenic plant of the present invention, wherein the seed is transgenic and comprises a heterologous nucleic acid construct of the present invention.

BRIEF DESCRIPTION OF THE FIGURES

FIG. 2 further shows the resulting constructs in a transgenic hybrid following cross-pollination of two plants, each transformed with one of the constructs shown. Ubi is rice ubiquitin promoter; FRT is the target site for the recombinase FLP; Cre is a site-specific recombinase; 35S is the 35S promoter from CaMV; hyg is the nucleotide sequence encoding resistance to the antibiotic, hygromycin; HS is the soybean heat shock promoter Gmhsp 17.5-E; gusA is a reporter gene or coding sequence encoding β-glucuronidase; loxP is the target site for the recombinase Cre; FLP is a site specific recombinase and gfp is a reporter gene or coding sequence that encodes green fluorescent protein (GFP).

DETAILED DESCRIPTION

Figure 1:
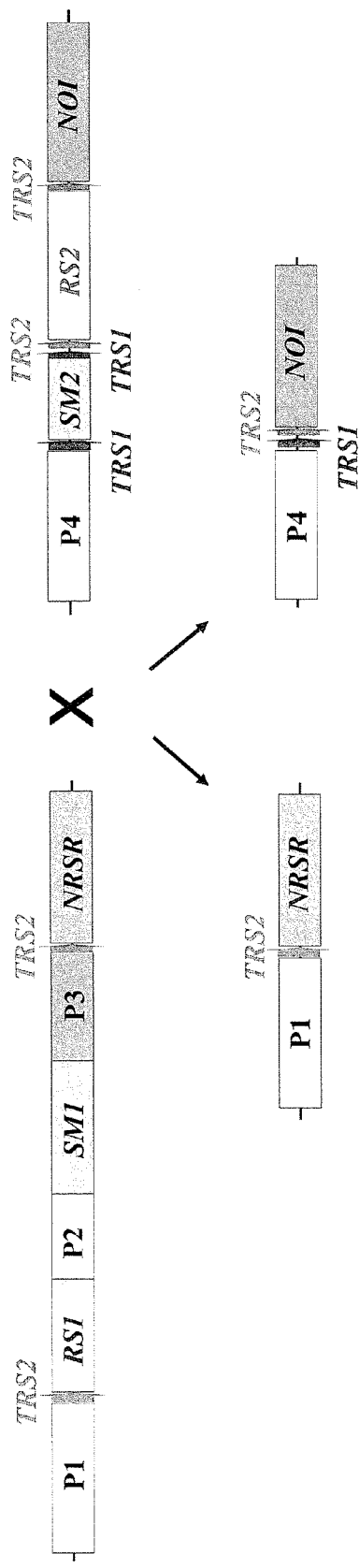
FIG. 1 shows two exemplary nucleic acid constructs of the present invention useful in the production of transgenic plant lines and the resulting constructs in a transgenic hybrid following cross-pollination of two plants, each transformed with one of the constructs shown. P1, P2, P3 and P4 are promoters; TSR1 and TRS2 are target sites, respectively; RS1 and RS2 are specific recombinases; SM1 and SM2 are selectable markers; NRSR is a nucleotide sequence the expression of which results in no or reduced sexual reproduction and NOI is at least one nucleotide sequence of interest.

The present invention will now be described more fully hereinafter with reference to the accompanying drawings and specification, in which preferred embodiments of the invention are shown. This invention may, however, be embodied in different forms and should not be construed as limited to the embodiments set forth herein.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of dose (e.g., an amount of a non-viral vector) and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP §2111.03. Thus, the term "consisting essentially of" when used in a claim of this invention is not intended to be interpreted to be equivalent to "comprising."

A used herein a "recombinase system" refers to a particular recombinase and its respective target site. Accordingly, one example of a recombinase system would be the FLP recombinase and its target site FRT.

The term "nucleotide sequence" refers to a heteropolymer of nucleotides or the sequence of these nucleotides from the 5' to 3' end of a nucleic acid molecule and includes DNA or RNA molecules, including cDNA, a DNA fragment, genomic DNA, synthetic (e.g., chemically synthesized) DNA, plasmid DNA, mRNA, and anti-sense RNA, any of which can be single stranded or double stranded. The terms "nucleotide sequence" "nucleic acid," "oligonucleotide" and "polynucleotide" are also used interchangeably herein to refer to a heteropolymer of nucleotides.

Nucleic acids of this invention can comprise a nucleotide sequence that can be identical in sequence to the sequence which is naturally occurring or, due to the well-characterized degeneracy of the nucleic acid code, can include alternative codons that encode the same amino acid as that which is found in the naturally occurring sequence. Furthermore, nucleic acids of this invention can comprise nucleotide sequences that can include codons which represent conservative substitutions of amino acids as are well known in the art, such that the biological activity of the resulting polypeptide and/or fragment is retained. A nucleic acid of this invention can be single or double stranded. Additionally, the nucleic acids of this invention can also include a nucleic acid strand that is partially complementary to a part of the nucleic acid sequence or completely complementary across the full length of the nucleic acid sequence. Nucleic acid sequences provided herein are presented herein in the 5' to 3' direction, from left to right and are represented using the standard code for representing the nucleotide characters as set forth in the U.S. sequence rules, 37 CFR §§1.821-1.825 and the World Intellectual Property Organization (WIPO) Standard ST.25.

As used herein, the term "gene" refers to a nucleic acid molecule capable of being used to produce mRNA or antisense RNA. Genes may or may not be capable of being used to produce a functional protein. Genes include both protein-coding and non-coding regions (e.g., introns, regulatory elements, and 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid. An "isolated" nucleic acid of the present invention is generally free of nucleic acid sequences that flank the nucleic acid of interest in the genomic DNA of the organism from which the nucleic acid was derived (such as coding sequences present at the 5' or 3' ends). However, the nucleic acid of this invention can include some additional bases or moieties that do not deleteriously affect the basic structural and/or functional characteristics of the nucleic acid. "Isolated" does not mean that the preparation is technically pure (homogeneous).

The term "transgene" as used herein, refers to any nucleic acid sequence used in the transformation of a plant or other organism. Thus, a transgene can be a coding sequence, a non-coding sequence, a cDNA, a gene or fragment or portion thereof, a genomic sequence, a regulatory element and the like.

The term "antisense" or "antigene" as used herein, refers to any composition containing a nucleotide sequence that is either fully or partially complementary to, and hybridize with, a specific DNA or RNA sequence. The term "antisense strand" is used in reference to a nucleic acid strand that is complementary to the "sense" strand. Antisense molecules include peptide nucleic acids (PNAs) and may be produced by any method including synthesis, restriction enzyme digestion and/or transcription. Once introduced into a cell, the complementary nucleic acid sequence combines with nucleic acid sequence(s) present in the cell (e.g., as an endogenous or exogenous sequence(s)) to form a duplex thereby preventing or minimizing transcription and/or translation. The designation "negative" is sometimes used in reference to the antisense strand, and "positive" is sometimes used in reference to the sense strand. An antigene sequence can be used to form a hybridization complex at the site of a noncoding region of a gene, thereby modulating expression of the gene (e.g., by enhancing or repressing transcription of the gene).

The term "RNAi" refers to RNA interference. The process involves the introduction of RNA into a cell that inhibits the expression of a gene. Also known as RNA silencing, inhibitory RNA, and RNA inactivation. RNAi as used herein includes double stranded (dsRNA), small interfering RNA (siRNA), small hairpin RNA (or short hairpin RNA) (shRNA) and microRNA (miRNA).

The terms "complementary" or "complementarity," as used herein, refer to the natural binding of polynucleotides under permissive salt and temperature conditions by base-pairing. For example, the sequence "A-G-T" binds to the complementary sequence "T-C-A." Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins.

As used herein "sequence identity" refers to the extent to which two optimally aligned polynucleotide or peptide sequences are invariant throughout a window of alignment of components, e.g., nucleotides or amino acids. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Adv. Appl. Math.*, 2:482-489, 1981, Smith et al., *Nucleic Acids Res.* 11:2205-2220, 1983).

Useful methods for determining sequence identity are also disclosed in Guide to Huge Computers (Martin J. Bishop, ed., Academic Press, San Diego (1994)), and Carillo, H., and Lipton, D., (*Applied Math* 48:1073 (1988)). More particularly, preferred computer programs for determining sequence identity include but are not limited to the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; (Altschul et al., *J Mol. Biol.* 215:403-410 (1990)); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity.

A first aspect of the present invention is a method of producing a transgenic hybrid plant having no or reduced sexual reproduction, the method comprising: (a) stably transforming a first plant with a first nucleic acid construct comprising: (i) a promoter, P1; (ii) a site specific recombinase, RS1; (iii) a promoter, P2; (iv) a selectable marker, SM1; (v) a promoter P3; (vi) at least one nucleotide sequence the expression of which results in no or reduced sexual reproduction, NRSR; and (vii) at least two target sites, TRS2, specific for a site specific recombinase, RS2, that is different from the site specific recombinase, RS1, and further wherein P1 is operably located upstream of RS1, P2 is operably located upstream of SM1, P3 is operably located upstream of NRSR, a first TRS2 is located immediately downstream of P1 and a second TRS2 is located upstream of NRSR; (b) stably transforming a second plant with a second nucleic acid construct comprising: (i) a promoter, P4; (ii) a site specific recombinase, RS2, that is different from the site specific recombinase, RS1, of (a); (iii) a selectable marker, SM2; (iv) at least one nucleotide sequence of interest, NOI; (v) at least two target sites, TRS1, specific for the site specific recombinase, RS1; and (vi) at least two target sites, TRS2, specific for the site specific recombinase, RS2, and further wherein P4 is operably located upstream of SM2, RS2 is located downstream of SM2, a first TRS1 is located immediately downstream of P4, a second TRS1 is located immediately downstream of SM2, a first TRS2 is located immediately upstream of RS2 and downstream of the second TRS1, a second TRS2 is located immediately downstream of RS2 and the NOI is located immediately downstream of the second TRS2; and (c) cross-pollinating the stably transformed first plant of (a) with the stably transformed second plant of (b) to produce a transgenic hybrid plant having no or reduced sexual reproduction. The nucleic acid constructs as described above are exemplified in FIG. 1.

Plants of the present invention can include any plant into which a transgene can be introduced. Accordingly, in one embodiment the first plant and/or the second plant of this invention includes, but is not limited to, angiosperms, gymnosperms, bryophytes, ferns and/or fern allies. For example, in particular embodiments, the first plant and/or the second plant can be an angiosperm. In other embodiments, the first plant and/or the second plant can be a monocot. In yet other embodiments, the first plant and/or the second plant can be a dicot. In still further embodiments of the present invention, the first plant and/or the second plant can be a turfgrass. In specific embodiments, the first plant and/or the second plant can be a creeping bent grass. In some embodiments, the first plant and the second plant are the same. In other embodiments, the first plant and the second plant are different. Accordingly, the first and second plant can be of the same or different species, genus, etc., as long as the first and second plants can be cross-pollinated.

The term "transformation" as used herein refers to the introduction of a heterologous nucleic acid into a cell. Transformation of a cell may be stable or transient. The term "transient transformation" or "transiently transformed" refers to the introduction of one or more heterologous nucleic acids into a cell wherein the heterologous nucleic acid is not heritable from one generation to another.

"Stable transformation" or "stably transformed" refers to the integration of the heterologous nucleic acid into the genome of the plant or incorporation of the heterologous nucleic acid into the cell or cells of the plant (e.g., via a plasmid) such that the heterologous nucleic acid is heritable across repeated generations. Thus, in one embodiment of the present invention a stably transformed plant is produced.

Transient transformation may be detected by, for example, an enzyme-linked immunosorbent assay (ELISA), which can detect the presence of a polypeptide encoded by one or more transgene introduced into a plant. Stable transformation of a cell can be detected by, for example, a Southern blot hybridization assay of genomic DNA of the cell with nucleic acid sequences which specifically hybridize with a nucleotide sequence of a transgene introduced into a plant. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods A nucleotide sequence of this invention can be introduced into a plant cell by any method known to those of skill in the art. Procedures for transforming a wide variety of plant species are well known and routine in the art and described throughout the literature. Such methods include, but are not limited to, transformation via bacterial-mediated nucleic acid delivery (e.g., via *Agrobacteria*), viral-mediated nucleic acid delivery, silicon carbide or nucleic acid whisker-mediated nucleic acid delivery, liposome mediated nucleic acid delivery, microinjection, microparticle bombardment, electroporation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

Bacterial mediated nucleic acid delivery includes but is not limited to DNA delivery by *Agrobacterium* spp. and is described, for example, in Horsch et al. (*Science* 227:1229 (1985); Ishida et al. (*Nature Biotechnol.* 14:745 750 (1996); and Fraley et al. (*Proc. Natl. Acad. Sci.* 80: 4803 (1983)). Transformation by various other bacterial species is described, for example, in Broothaerts et al. (*Nature* 433:629-633 (2005)).

Physical delivery of nucleotide sequences via microparticle bombardment is also well known and is described, for example, in Sanford et al. (*Methods in Enzymology* 217:483-509 (1993)) and McCabe et al. (*Plant Cell Tiss. Org. Cult.* 33:227-236 (1993)).

Another method for physical delivery of nucleic acid to plants is sonication of target cells. This method is described, for example, in Zhang et al. (*Bio/Technology* 9:996 (1991)). Nanoparticle-mediated transformation is another method for delivery of nucleic acids into plant cells (Radu et al., *J. Am. Chem. Soc.* 126: 13216-13217 (2004); Torney, et al. *Society for In Vitro Biology*, Minneapolis, Minn. (2006)). Alternatively, liposome or spheroplast fusion can be used to introduce nucleotide sequences into plants. Examples of the use of liposome or spheroplast fusion are provided, for example, in Deshayes et al. (*EMBO J.*, 4:2731 (1985), and Christou et al. (*Proc Natl. Acad. Sci. U.S.A.* 84:3962 (1987)). Direct uptake of nucleic acid into protoplasts using $CaCl_2$ precipitation, polyvinyl alcohol or poly-L-ornithine is described, for example, in Hain et al. (*Mol. Gen. Genet.* 199:161 (1985)) and Draper et al. (*Plant Cell Physiol.* 23:451 (1982)). Electroporation of protoplasts and whole cells and tissues is described, for example, in Donn et al. (In *Abstracts of VIIth International Congress on Plant Cell and Tissue Culture IAPTC*, A2-38, p 53 (1990); D'Halluin et al. (*Plant Cell* 4:1495-1505 (1992)); Spencer et al. (*Plant Mol. Biol.* 24:51-61 (1994)) and Fromm et al. (*Proc. Natl. Acad. Sci.* 82: 5824 (1985)). Polyethylene glycol (PEG) precipitation is described, for example, in Paszkowski et al. (*EMBO J.* 3:2717 2722 (1984)). Microinjection of plant cell protoplasts or embryogenic callus is described, for example, in Crossway (*Mol. Gen. Genetics* 202:179-185 (1985)). Silicon carbide whisker methodology is described, for example, in Dunwell et al. (*Methods Mol. Biol.* 111:375-382 (1999)); Frame et al. (*Plant J.* 6:941-948 (1994)); and Kaeppler et al. (*Plant Cell Rep.* 9:415-418 (1990)).

In addition to these various methods of introducing nucleotide sequences into plant cells, expression vectors and in vitro culture methods for plant cell or tissue transformation and regeneration of plants are also well known in the art and are available for carrying out the methods of this invention. See, for example, Gruber et al. ("Vectors for Plant Transformation" in *Methods in Plant Molecular Biology and Biotechnology*, Glick, B. R. and Thompson, J. E., Eds. (CRC Press, Inc., Boca Raton, (1993), pages 89-119).

The term "vector" refers to a composition for transferring, delivering or introducing a nucleic acid (or nucleic acids) into a cell. A vector comprises a nucleic acid comprising the nucleotide sequence to be transferred, delivered or introduced. In some embodiments, a vector of this invention can be a viral vector, which can comprise, e.g., a viral capsid and/or other materials for facilitating entry of the nucleic acid into a cell and/or replication of the nucleic acid of the vector in the cell (e.g., reverse transcriptase or other enzymes which are packaged within the capsid, or as part of the capsid). The viral vector can be an infectious virus particle that delivers nucleic acid into a cell following infection of the cell by the virus particle.

A plant cell of this invention can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)). Methods of selecting for transformed transgenic plants, plant cells and/or plant tissue culture are routine in the art and can be employed in the methods of the invention provided herein.

A large variety of plants have been shown to be capable of regeneration from transformed individual cells to obtain transgenic plants. Those of skill in the art can optimize the particular conditions for transformation, selection and regeneration according to these art-known methods. Factors that affect the efficiency of transformation include the species of plant, the tissue infected, composition of the medium for tissue culture, selectable marker coding sequences, the length of any of the steps of the methods described herein, the kinds of vectors, and/or light/dark conditions. Therefore, these and other factors can be varied to determine the optimal transformation protocol for any particular plant species. It is recognized that not every species will react in the same manner to the transformation conditions and may require a slightly different modification of the protocols disclosed herein. However, by altering each of the variables according to methods routine in the art, an optimum protocol can be derived for any plant species.

Accordingly, in one embodiment, a heterologous nucleotide sequence is introduced into a cell of a plant of the present invention by co-cultivation of the cell with *Agrobacterium tumefaciens* to produce a transgenic plant. In a further embodiment, a heterologous nucleotide sequence is introduced into a cell of a plant of the present invention by direct nucleic acid transfer to produce a transgenic plant.

As used herein, the term "promoter" refers to a region of a nucleotide sequence that incorporates the necessary signals for the efficient expression of a coding sequence. This may include sequences to which an RNA polymerase binds, but is not limited to such sequences and can include regions to which other regulatory proteins bind together with regions involved in the control of protein translation and can also include coding sequences.

A "plant promoter" of this invention is a promoter capable of initiating transcription in plant cells. Such promoters include those that drive expression of a nucleotide sequence constitutively, those that drive expression when induced, and those that drive expression in a tissue- or developmentally specific manner, as these various types of promoters are known in the art.

Thus, for example, in some embodiments of the invention, a constitutive promoter can be used to drive the expression of a transgene of this invention in a plant cell. A constitutive promoter is an unregulated promoter that allows for continual transcription of its associated gene or coding sequence. Thus, constitutive promoters are generally active under most environmental conditions, in most or all cell types and in most or all states of development or cell differentiation.

Any constitutive promoter functional in a plant can be utilized in the instant invention. Exemplary constitutive promoters include, but are not limited to, the promoters from plant viruses including, but not limited to, the 35S promoter from CaMV (Odell et al., *Nature* 313: 810 (1985)); figwort mosaic virus (FMV) 35S promoter (P-FMV35S, U.S. Pat. Nos. 6,051,753 and 6,018,100); the enhanced CaMV35S promoter (e35S); the 1'- or 2'-promoter derived from T-DNA of *Agrobacterium tumefaciens*; the nopaline synthase (NOS) and/or octopine synthase (OCS) promoters, which are carried on tumor-inducing plasmids of *Agrobacterium tumefaciens* (Ebert et al., *Proc. Natl. Acad. Sci.* (U.S.A.), 84:5745 5749, 1987); actin promoters including, but not limited to, rice actin (McElroy et al., *Plant Cell* 2: 163 (1990); U.S. Pat. No. 5,641,876); histone promoters; tubulin promoters; ubiquitin and polyubiquitin promoters ((Sun and Callis, *Plant J.*, 11(5):

1017-1027 (1997)); Christensen et al., *Plant Mol. Biol.* 12: 619 (1989) and Christensen et al., *Plant Mol. Biol.* 18: 675 (1992)); pEMU (Last et al., *Theor. Appl. Genet.* 81: 581 (1991)); the mannopine synthase promoter (MAS) (Velten et al., *EMBO J.* 3: 2723 (1984)); maize H3 histone (Lepelit et al., *Mol. Gen. Genet.* 231: 276 (1992) and Atanassova et al., *Plant Journal* 2: 291 (1992)); the ALS promoter, a XbaI/NcoI fragment 5' to the *Brassica napus* ALS3 structural gene (or a nucleotide sequence that has substantial sequence similarity to said XbaI/NcoI fragment); ACT11 from *Arabidopsis* (Huang et al., *Plant Mol. Biol.* 33:125-139 (1996)); Cat3 from *Arabidopsis* (GenBank No. U43147, Zhong et al., *Mol. Gen. Genet.* 251:196-203 (1996)); GPc1 from maize (GenBank No. X15596, Martinez et al., *J. Mol. Biol.* 208:551-565 (1989)); and Gpc2 from maize (GenBank No. U45855, Manjunath et al., *Plant Mol. Biol.* 33:97-112 (1997)).

In some embodiments of the present invention, an inducible promoter can be used to drive the expression of a transgene. Inducible promoters activate or initiate expression only after exposure to, or contact with, an inducing agent. Inducing agents include, but are not limited to, various environmental conditions (e.g., pH, temperature), proteins and chemicals. Examples of environmental conditions that can affect transcription by inducible promoters include pathogen attack, anaerobic conditions, extreme temperature and/or the presence of light. Examples of chemical inducing agents include, but are not limited to, herbicides, antibiotics, ethanol, plant hormones and steroids. Any inducible promoter that is functional in a plant can be used in the instant invention (see, Ward et al., (1993) *Plant Mol. Biol.* 22: 361 (1993)). Exemplary inducible promoters include, but are not limited to, that from the ACEI system, which responds to copper (Melt et al., *PNAS* 90: 4567 (1993)); the ln2 gene from maize, which responds to benzenesulfonamide herbicide safeners (Hershey et al., (1991) *Mol. Gen. Genetics* 227: 229 (1991) and Gatz et al., *Mol. Gen. Genetics* 243: 32 (1994)); a heat shock promoter, including, but not limited to, the soybean heat shock promoters Gmhsp 17.5-E, Gmhsp 17.2-E and Gmhsp 17.6-L and those described in U.S. Pat. No. 5,447,858; the Tet repressor from Tn10 (Gatz et al., *Mol. Gen. Genet.* 227: 229 (1991)) and the light-inducible promoter from the small subunit of ribulose bisphosphate carboxylase (ssRUBISCO). Other examples of inducible promoters include, but are not limited to, those described by Moore et al. (*Plant J.* 45:651-683 (2006)). Additionally, some inducible promoters respond to an inducing agent to which plants do not normally respond. An example of such an inducible promoter is the inducible promoter from a steroid hormone gene, the transcriptional activity of which is induced by a glucocorticosteroid hormone (Schena et al., *Proc. Natl. Acad. Sci. U.S.A.* 88: 421 (1991)).

In further embodiments of the present invention, a tissue-specific promoter can be used to drive the expression of a transgene in a particular tissue in the transgenic plant. Tissue-specific promoters drive expression of a nucleic acid only in certain tissues or cell types, e.g., in the case of plants, in the leaves, stems, flowers and their various parts, roots, fruits and/or seeds, etc. Thus, plants transformed with a nucleic acid of interest operably linked to a tissue-specific promoter produce the product encoded by the transgene exclusively, or preferentially, in a specific tissue or cell type.

Any plant tissue-specific promoter can be utilized in the instant invention. Exemplary tissue-specific promoters include, but are not limited to, a root-specific promoter, such as that from the phaseolin gene (Murai et al., *Science* 23: 476 (1983) and Sengupta-Gopalan et al., *Proc. Natl. Acad. Sci. USA* 82: 3320 (1985)); a leaf-specific and light-induced promoter such as that from cab or rubisco (Simpson et al. *EMBO J.* 4: 2723 (1985) and Timko et al., *Nature* 318: 579 (1985)); the fruit-specific E8 promoter from tomato (Lincoln et al. *Proc. Nat'l. Acad. Sci. USA* 84: 2793-2797 (1988); Deikman et al. *EMBO J.* 7: 3315-3320 (1988); Deikman et al. *Plant Physiol.* 100: 2013-2017 (1992); seed-specific promoters of, for example, *Arabidopsis thaliana* (Krebbers et al. (1988) *Plant Physiol.* 87:859); an anther-specific promoter such as that from LAT52 (Twell et al. *Mol. Gen. Genet.* 217: 240 (1989)) or European Patent Application No 344029, and those described by Xu et al. (*Plant Cell Rep.* 25:231-240 (2006)) and Gomez et al. (*Planta* 219:967-981 (2004)); a pollen-specific promoter such as that from Zm13 (Guerrero et al., *Mol. Gen. Genet.* 224: 161 (1993)), and those described by Yamaji et al. (*Plant Cell Rep.* 25:749-57 (2006)) and Okada et al. (*Plant Cell Physiol.* 46:749-802 (2005)); a pith-specific promoter, such as the promoter isolated from a plant TrpA gene as described in International PCT Publication No. WO93/07278; and a microspore-specific promoter such as that from apg (Twell et al. *Sex. Plant Reprod.* 6: 217 (1993)). Exemplary green tissue-specific promoters include the maize phosphoenol pyruvate carboxylase (PEPC) promoter, small subunit ribulose bis-carboxylase promoters (ssRUBISCO) and the chlorophyll a/b binding protein promoters.

A promoter of the present invention can also be developmentally specific in that it drives expression during a particular "developmental phase" of the plant. Thus, such a promoter is capable of directing selective expression of a nucleotide sequence of interest at a particular period or phase in the life of a plant (e.g., seed formation), compared to the relative absence of expression of the same nucleotide sequence of interest in a different phase (e.g. seed germination). For example, in plants, seed-specific promoters are typically active during the development of seeds and germination promoters are typically active during germination of the seeds. Any developmentally-specific promoter capable of functioning in a plant can be used in the present invention.

The promoters, P1 and P4, of the present invention can be any promoter capable of initiating expression of a nucleotide sequence in a plant cell. Thus, P1 and/or P4 can be any constitutive, inducible and/or tissue- or developmentally specific promoter that is functional in a plant cell. Further, P1 and P4 can be the same promoter or they can be different promoters. In one embodiment, the P1 and P4 promoters are both the rice ubiquitin promoter.

The promoter, P2, of the present invention can be any constitutive promoter that is functional in expressing a nucleotide sequence in a plant cell. Thus, P2 can be the 35S promoter from CaMV, a ubiquitin promoter, an actin promoter, etc. In particular embodiments of the present invention, P2 is the 35S promoter.

The promoter, P3, of the present invention can be any inducible promoter functional in expressing a nucleotide sequence in a plant cell when induced. Thus, in various embodiments of the present invention, P3 can be a heat shock promoter, which can include, but is not limited to, Gmhsp 17.5-E, Gmhsp 17.2-E, Gmhsp 17.6-L, and any combination thereof. In some embodiments, P3 is Gmhsp 17.5-E.

A "site-specific recombinase" as used herein refers to an enzyme that catalyzes recombination between specific recombination sites, referred to herein as "target sites." Recombinases exert their effects by promoting recombination between recombining or target sites specific for a given recombinase. The target sites can be inverted and/or direct repeats of one another and are specific for the particular site-specific recombinase. Recombination between directly oriented target sites on a circular molecule leads to excision of the nucleotide sequence between them, whereas recombination between sites on separate molecules produces a co-integration event. Recombination between inverted target sites results in inversion of the intervening nucleotide sequence.

Site-specific recombinases and their respective target sites that are useful in the present invention include, but are not limited to, FLP/FRT, Cre/lox, R/RS, Gin/gix, Tn3 recombinase, recombinase of transposon gamma/delta, the recombinase from transposon mariner, or any other site-specific recombinase that is functional in a plant. These recombinase systems can be present in a nucleic acid construct of this invention in any combination and/or can be divided among constructs (e.g., a Cre encoding nucleotide sequence can be present in one nucleic acid construct and its respective lox sites on a separate nucleic acid construct).

The present invention provides a coordinated excisional nucleic acid recombination system utilizing at least two different recombinases to achieve excision of unwanted transgenic nucleotide sequences, while at the same time allowing nucleotide sequence(s) of interest to be expressed in the transgenic plant. Thus, one embodiment of the invention provides a hybrid plant that is the result of cross-pollination between two stably transformed plants, each of the stably transformed plants comprising a nucleic acid construct having at least one recombinase coding sequence. In some embodiments, the respective nucleic acid constructs in the first and second stably transformed plants each comprise one recombinase coding sequence. In other embodiments, one or both of the respective nucleic acid constructs each comprise two or more recombinase coding sequences.

In one embodiment of the present invention, the first recombinase, RS1, of the first nucleic acid construct can be FLP, Cre, R, or Gin. In an additional embodiment of the invention, the second recombinase, RS2, of the second nucleic acid construct, can be FLP, Cre, R, or Gin. The target sites of the respective recombinases are specific for each recombinase. Thus, for example, the target site for FLP is FRT, the target site for Cre is 10× or loxP, the target site for R is RS and the target site for Gin is gix, etc, as is known in the art. Therefore, the target sites of the present invention, TRS1 and TRS2, are chosen based on which recombinase is selected. The target sites, TRS1 and TRS2, are then placed within the nucleic acid constructs of this invention in positions that allow the recombinase to function according to the invention described herein.

In some embodiments of the present invention, the recombinases in each of the stably transformed plants are different from one another. For example, when the RS1 of the first nucleic acid construct is FLP, then the RS2 of the second nucleic acid construct can be Cre, R, or Gin, or any other recombinase functional in the plant except FLP. Alternatively, if the RS1 of the first nucleic acid construct is Cre, then the RS2 of the second nucleic acid construct can be FLP, R, or Gin, or any recombinase functional in the plant except Cre. If the RS1 of the first nucleic acid construct is R, then the RS2 of the second nucleic acid construct can be FLP, Cre, or Gin, or any recombinase functional in the plant except R. Further, if the RS1 of the first nucleic acid construct is Gin, then the RS2 of the second nucleic acid construct can be FLP, Cre, or R, or any recombinase functional in the plant except Gin, and so on.

In an exemplary embodiment of the present invention, the first nucleic acid construct comprises a nucleotide sequence encoding a recombinase, RS1, and the second nucleic acid construct comprises a nucleotide sequence encoding a different recombinase, RS2, wherein RS1 is Cre and RS2 is FLP. Alternatively, in a further embodiment RS1 is FLP and RS2 is Cre.

The nucleic acid constructs of the present invention can further comprise a nucleotide sequence encoding a selectable marker, operably linked to a regulatory element (a promoter, for example) that allows transformed cells in which the expression product of the selectable marker sequence is produced, to be recovered by either negative selection, i.e., inhibiting growth of cells that do not contain the selectable marker, or positive selection, i.e., screening for the product encoded by the selectable marker coding sequence. Many commonly used selectable marker coding sequences for plant transformation are well known in the transformation art, and include, for example, nucleotide sequences that code for enzymes that metabolically detoxify a selective chemical agent which may be an antibiotic or a herbicide, and/or nucleotide sequences that encode an altered target which is insensitive to the inhibitor (See e.g., Aragão et al., *Braz. J. Plant Physiol.* 14: 1-10 (2002)). Any nucleotide sequence encoding a selectable marker that can be expressed in a plant is useful in the present invention.

One commonly used selectable marker coding sequence for plant transformation is the nucleotide sequence encoding neomycin phosphotransferase II (npfII), isolated from transposon Tn5, which when placed under the control of plant regulatory signals confers resistance to kanamycin (Fraley et al., *Proc. Natl. Acad. Sci. U.S.A.*, 80: 4803 (1983)). Another commonly used selectable marker coding sequence encodes hygromycin phosphotransferase, which confers resistance to the antibiotic hygromycin (Vanden Elzen et al., *Plant Mol. Biol.*, 5: 299 (1985)).

Some selectable marker coding sequences confer resistance to herbicides. Herbicide resistance sequences generally encode a modified target protein insensitive to the herbicide or an enzyme that degrades or detoxifies the herbicide in the plant before it can act (DeBlock et al., *EMBO J.* 6, 2513 (1987); DeBlock et al., *Plant Physiol.* 91, 691 (1989); Fromm et al., *BioTechnology* 8, 833 (1990); Gordon-Kamm et al., *Plant Cell* 2, 603 (1990)). For example, resistance to glyphosphate or sulfonylurea herbicides has been obtained using marker sequences coding for the mutant target enzymes, 5-enolpyruvylshikimate-3-phosphate synthase (EPSPS) and acetolactate synthase (ALS). Resistance to glufosinate ammonium, bromoxynil, and 2,4-dichlorophenoxyacetate (2,4-D) have been obtained by using bacterial nucleotide sequences encoding phosphinothricin acetyltransferase, a nitrilase, or a 2,4-dichlorophenoxyacetate monooxygenase, which detoxify the respective herbicides.

Other selectable marker coding sequences for plant transformation are not of bacterial origin. These coding sequences include, for example, mouse dihydrofolate reductase, plant 5-eno/pyruvylshikimate-3-phosphate synthase and plant acetolactate synthase (Eichholtz et al., *Somatic Cell Mol. Genet.* 13: 67 (1987); Shah et al., *Science* 233: 478 (1986); Charest et al., *Plant Cell Rep.* 8: 643 (1990)).

Another class of marker coding sequences for plant transformation requires screening of presumptively transformed plant cells rather than direct genetic selection of transformed cells for resistance to a toxic substance such as an antibiotic. These coding sequences are particularly useful to quantify or visualize the spatial pattern of expression of a nucleotide sequence in specific tissues and are frequently referred to as reporter nucleotide sequences because they can be fused to a gene or gene regulatory sequence for the investigation of gene expression. Commonly used nucleotide sequences for screening presumptively transformed cells include, but are not limited to, those encoding β-glucuronidase (GUS), β-galactosidase, luciferase and chloramphenicol acetyltransferase (Jefferson *Plant Mol. Biol, Rep.* 5:387 (1987); Teeri et al.

EMBO J 8:343 (1989); Koncz et al. *Proc. Natl. Acad. Sci. U.S.A.* 84:131 (1987); De Block et al. *EMBO J.* 3:1681 (1984)).

Some in vivo methods for detecting GUS activity that do not require destruction of plant tissue are available (e.g., Molecular Probes Publication 2908, Imagene Green™, p. 1-4 (1993) and Naleway et al., *J. Cell Biol.* 115:15 (1991)). In addition, a nucleotide sequence encoding green fluorescent protein (GFP) has been utilized as a marker for expression in prokaryotic and eukaryotic cells (Chalfie et al., *Science* 263: 802 (1994)). GFP and mutants of GFP may be used as screenable markers. Similar to GFP, red fluorescent protein (DsRed2) has also been used as a selectable marker in plants (Nishizawa et al., *Plant Cell Reports* 25 (12): 1355-1361 (2006)). In addition, reef coral proteins have been used as selectable markers in plants (Wenck et al. *Plant Cell Reports* 22(4):244-251 (2003)).

For purposes of the present invention, selectable marker coding sequences can also include, but are not limited to, nucleotide sequences encoding: neomycin phosphotransferase I and II (Southern et al., *J. Mol. Appl. Gen.* 1:327 (1982)); Fraley et al., *CRC Critical Reviews in Plant Science* 4:1 (1986)); cyanamide hydratase (Maier-Greiner et al., *Proc. Natl. Acad. Sci. USA* 88:4250 (1991)); aspartate kinase; dihydrodipicolinate synthase (Perl et al., *BioTechnology* 11, 715 (1993)); bar gene (Toki et al., *Plant Physiol.* 100:1503 (1992); Meagher et al., *Crop Sci.* 36:1367 (1996)); tryptophane decarboxylase (Goddijn et al., *Plant Mol. Biol.* 22:907 (1993)); hygromycin phosphotransferase (HPT or HYG; Shimizu et al., *Mol. Cell. Biol.* 6:1074 (1986); Waldron et al., *Plant Mol. Biol.* 5:103 (1985); Zhijian et al., *Plant Science* 108:219 (1995)); dihydrofolate reductase (DHFR; Kwok et al., *Proc. Natl. Acad. Sci. USA* 83:4552 (1986)); phosphinothricin acetyltransferase (DeBlock et al., *EMBO J.* 6:2513 (1987)); 2,2-dichloropropionic acid dehalogenase (Buchanan-Wollatron et al., *J. Cell. Biochem.* 13D:330 (1989)); acetohydroxyacid synthase (U.S. Pat. No. 4,761,373 to Anderson et al.; Haughn et al., *Mol. Gen. Genet.* 221:266 (1988)); 5-enolpyruvyl-shikimate-phosphate synthase (aroA; Comai et al., *Nature* 317:741 (1985)); haloarylnitrilase (PCT Publication No. WO 87/04181 to Stalker et al.); acetyl-coenzyme A carboxylase (Parker et al., *Plant Physiol.* 92:1220 (1990)); dihydropteroate synthase (sulI; Guerineau et al., *Plant Mol. Biol.* 15:127 (1990)); and 32 kDa photosystem II polypeptide (psbA; Hirschberg et al., *Science* 222: 1346 (1983)).

Also included are nucleotide sequences that encode polypeptides that confer resistance to: gentamicin (Miki et al., *J. Biotechnol.* 107:193-232 (2004)); chloramphenicol (Herrera-Estrella et al., *EMBO J.* 2:987 (1983)); methotrexate (Herrera-Estrella et al., *Nature* 303:209 (1983); Meijer et al., *Plant Mol. Biol.* 16:807 (1991)); Meijer et al., *Plant Mol. Bio.* 16:807 (1991)); streptomycin (Jones et al., *Mol. Gen. Genet.* 210:86 (1987)); spectinomycin (Bretagne-Sagnard et al., *Transgenic Res.* 5:131 (1996)); bleomycin (Hille et al., *Plant Mol. Biol.* 7, 171 (1986)); sulfonamide (Guerineau et al., *Plant Mol. Bio.* 15:127 (1990); bromoxynil (Stalker et al., *Science* 242:419 (1988)); 2,4-D (Streber et al., *Bio/Technology* 7, 811 (1989)); phosphinothricin (DeBlock et al., *EMBO J.* 6:2513 (1987)); and/or spectinomycin (Bretagne-Sagnard and Chupeau, *Transgenic Research* 5:131 (1996)).

The product of the bar gene confers herbicide resistance to glufosinate-type herbicides, such as phosphinothricin (PPT) or bialaphos, and the like. As noted above, other selectable markers that could be used in the nucleic acid constructs of the present invention include, but are not limited to, the pat gene or coding sequence, the expression of which also confers resistance to bialaphos and phosphinothricin resistance, the ALS gene or coding sequence for imidazolinone resistance, the HPH or HYG gene or coding sequence for hygromycin resistance, the EPSP synthase gene or coding sequence for glyphosate resistance, the Hm1 gene or coding sequence for resistance to the Hc-toxin, and/or other selective agents used routinely and known to one of ordinary skill in the art. See generally, Yarranton, *Curr. Opin. Biotech.* 3:506 (1992); Chistopherson et al., *Proc. Natl. Acad. Sci. USA* 89:6314 (1992); Yao et al., *Cell* 71:63 (1992); Reznikoff, *Mol. Microbiol.* 6:2419 (1992); Barkley et al., *The Operon* 177-220 (1980); Hu et al., *Cell* 48:555 (1987); Brown et al., *Cell* 49:603 (1987); Figge et al., *Cell* 52:713 (1988); Deuschle et al., *Proc. Natl. Acad. Sci. USA* 86:400 (1989); Fuerst et al., *Proc. Natl. Acad. Sci. USA* 86:2549 (1989); Deuschle et al., *Science* 248:480 (1990); Labow et al., *Mol. Cell. Biol.* 10:3343 (1990); Zambretti et al., *Proc. Natl. Acad. Sci. USA* 89:3952 (1992); Baim et al., *Proc. Natl. Acad. Sci. USA* 88:5072 (1991); Wyborski et al., *Nuc. Acids Res.* 19:4647 (1991); Hillenand-Wissman, *Topics in Mol. And Struc. Biol.* 10:143 (1989); Degenkolb et al., *Antimicrob. Agents Chemother.* 35:1591 (1991); Kleinschnidt et al., *Biochemistry* 27:1094 (1988); Gatz et al., *Plant J.* 2:397 (1992); Gossen et al., *Proc. Natl. Acad. Sci. USA* 89:5547 (1992); Oliva et al., *Antimicrob. Agents Chemother.* 36:913 (1992); Hlavka et al., *Handbook of Experimental Pharmacology* 78 (1985); and Gill et al., *Nature* 334:721 (1988).

Additionally, for purposes of the present invention, selectable markers include nucleotide sequence(s) conferring environmental or artificial stress resistance or tolerance including, but not limited to, a nucleotide sequence conferring high glucose tolerance, a nucleotide sequence conferring low phosphate tolerance, a nucleotide sequence conferring mannose tolerance, and/or a nucleotide sequence conferring drought tolerance, salt tolerance or cold tolerance. Examples of nucleotide sequences that conferring environmental or artificial stress resistance or tolerance include, but are not limited to, a nucleotide sequence encoding trehalose phosphate synthase, a nucleotide sequence encoding phophomannose isomerase (Negrotto et al., *Plant Cell Reports* 19(8):798-803 (2003)), a nucleotide sequence encoding the *Arabidopsis* vacuolar $H^+$-pyrophosphatase gene, AVP1, a nucleotide sequence conferring aldehyde resistance (U.S. Pat. No. 5,633,153), a nucleotide sequence conferring cyanamide resistance (Weeks et al., Crop Sci 40:1749-1754 (2000)) and those described by Iuchi et al. (*Plant J.* 27(4):325-332 (2001)); Umezawa et al. (*Curr Opin Biotechnol.* 17(2):113-22 (2006)); U.S. Pat. No. 5,837,545; Oraby et al. (*Crop Sci.* 45:2218-2227 (2005)) and Shi et al. (*Proc. Natl. Acad. Sci.* 97:6896-6901 (2000)).

The above list of selectable marker genes and coding sequences is not meant to be limiting as any selectable marker coding sequence now known or later identified can be used in the present invention. Also, a selectable marker of this invention can be used in any combination with any other selectable marker.

Accordingly, in one embodiment of the present invention, the first selectable marker, SM1, of the first nucleic acid construct is selected from the group consisting of a nucleotide sequence conferring antibiotic resistance, a nucleotide sequence conferring herbicide resistance or tolerance, a nucleotide sequence encoding a fluorescing protein, a nucleotide sequence encoding a hydrolyzing enzyme, a nucleotide sequence conferring environmental or artificial stress resistance or tolerance, a nucleotide sequence conferring the ability to metabolize a compound that causes toxicity in a plant that cannot metabolize the compound, a nucleotide sequence that encodes a nutritional deficiency, and any combination thereof. In a further embodiment, SM1 is a nucleotide sequence conferring antibiotic resistance, which can be, for example, a hyg, neo, tet, ble, kan, pur, amp or, aada gene or coding sequence and any combination thereof, as well as any other nucleotide sequence conferring antibiotic resistance now known or later identified. Thus, in some embodiments, the first selectable marker, SM1, can be the hyg gene or the equivalent coding sequence In an additional embodiment, the first selectable marker, SM1, is a nucleotide sequence conferring herbicide resistance or tolerance, which can be nucleotide sequences conferring resistance or tolerance to the herbicides bialaphos, glyphosate, sulfonylurea, glufosinate ammonium, bromoxynil, 2,4-dichlorophenoxyacetate, and any combination thereof, as well as any other nucleotide sequence conferring resistance to a herbicide now known or later identified. In another aspect of the invention, SM1 can be a nucleotide sequence conferring resistance or tolerance to bialaphos.

In yet a further aspect of the invention, the first nucleic acid construct can comprise a first selectable marker, SM1, wherein the SM1 is a nucleotide sequence encoding a fluorescing protein, which can be a nucleotide sequence that encodes green fluorescent protein, a nucleotide sequence that encodes luciferase, a nucleotide sequence that encodes red fluorescent protein, a nucleotide sequence that encodes reef-coral protein, and any combination thereof, as well as any other nucleotide sequence encoding a fluorescing protein now known or later identified.

In an additional embodiment, the first nucleic acid construct comprises a selectable marker, SM1, wherein SM1 is a nucleotide sequence conferring environmental or artificial stress resistance or tolerance. A nucleotide sequence conferring environmental or artificial stress resistance and/or tolerance includes, but is not limited to, a nucleotide sequence conferring high glucose tolerance, a nucleotide sequence conferring mannose tolerance, a nucleotide sequence conferring low phosphate tolerance, and/or a nucleotide sequence conferring drought tolerance, salt tolerance or cold tolerance, as well as any other nucleotide sequence conferring environmental or artificial stress resistance and/or tolerance now known or later identified. Accordingly, in one embodiment of the present invention, SM1 is a nucleotide sequence encoding trehalose phosphate synthase. In some embodiments of the present invention, SM1 is a nucleotide sequence encoding phophomannose isomerase. In other embodiments, SM1 is a nucleotide sequence conferring aldehyde resistance. In further embodiments of the present invention, SM1 is a nucleotide sequence conferring cyanamide resistance.

Another embodiment of the invention provides a first nucleic acid construct comprising a selectable marker, SM1, wherein SM1 is a nucleotide sequence encoding a hydrolyzing enzyme, further wherein SM1 can be a nucleotide sequence encoding β-galactosidase, a nucleotide sequence encoding β-glucuronidase, and any combination thereof, as well as any other nucleotide sequence encoding a hydrolyzing enzyme now known or later identified.

In a still further embodiment, the first nucleic acid construct of the invention can comprise a selectable marker, SM1, wherein the selectable marker, SM1, is a nucleotide sequence, the expression of which results in a nutritional deficiency in the plant. Thus, in some embodiments, SM1 can be a nucleotide sequence, the expression of which results in a uracil deficiency. In other embodiments, SM1 can be a nucleotide sequence, the expression of which results in a histidine deficiency. In still other embodiments, SM1 can be a nucleotide sequence, the expression of which results in a plant having a leucine deficiency. Any such nucleotide sequence, the expression of which results in a nutritional deficiency that is observable or detectable in a plant, as are well known in the art, can be used in the present invention.

The present invention further provides a second nucleic acid construct comprising a second selectable marker, SM2, which in some embodiments, can be a nucleotide sequence conferring antibiotic resistance, a nucleotide sequence conferring herbicide resistance or tolerance, a nucleotide sequence encoding a fluorescing protein, a nucleotide sequence encoding a hydrolyzing enzyme, a nucleotide sequence conferring environmental or artificial stress resistance or tolerance, a nucleotide sequence, the expression of which results in a nutritional deficiency, and any combination thereof. In a further embodiment, SM2 can be a nucleotide sequence conferring antibiotic resistance, which can be, e.g., a hyg, neo, tet, ble, kan, pur, amp, and/or aadA gene or equivalent coding sequence, and any combination thereof. Thus, in some embodiments, the second selectable marker, SM2, can be the hyg gene or coding sequence In further embodiments, the second selectable marker, SM2, can be a nucleotide sequence conferring herbicide resistance or tolerance, for example, to the herbicides bialaphos, glyphosate, sulfonylurea, glufosinate ammonium, bromoxynil, 2,4-dichlorophenoxyacetate, and any combination thereof. In certain aspects of the invention, the second selectable marker, SM2, can be a nucleotide sequence conferring resistance or tolerance to bialaphos.

In additional embodiments of the invention described herein, the second nucleic acid construct can comprises a second selectable marker, SM2, wherein the SM2 is a nucleotide sequence encoding a fluorescing protein, which can be a nucleotide sequence that encodes green fluorescent protein, a nucleotide sequence that encodes luciferase, a nucleotide sequence that encodes red fluorescent protein, a nucleotide sequence that encodes reef-coral protein, and any combination thereof, as well as any other nucleotide sequence encoding a fluorescing protein now known or later identified.

In an additional embodiment, the second nucleic acid construct comprises a selectable marker, SM2, wherein SM2 is a nucleotide sequence conferring environmental or artificial stress resistance or tolerance. A nucleotide sequence conferring environmental or artificial stress resistance or tolerance includes, but is not limited to, a nucleotide sequence conferring high glucose tolerance, a nucleotide sequence conferring low phosphate tolerance, a nucleotide sequence conferring mannose tolerance, and/or a nucleotide sequence conferring drought tolerance, salt tolerance or cold tolerance, as well as any other nucleotide sequence conferring environmental or artificial stress tolerance now known or later identified. Accordingly, in one embodiment of the present invention, SM2 is a nucleotide sequence encoding trehalose phosphate synthase. In some embodiments of the present invention, SM2 is a nucleotide sequence encoding phophomannose isomerase. In other embodiments, SM2 is a nucleotide sequence conferring aldehyde resistance. In further embodiments of the present invention, SM2 is a nucleotide sequence conferring cyanamide resistance.

Yet other embodiments of the invention provide a second nucleic acid construct comprising a second selectable marker, SM2, wherein SM2 encodes a hydrolyzing enzyme, which can be β-galactosidase, β-glucuronidase, and any combination thereof, as well as any other hydrolyzing enzyme now known or later identified.

In still further embodiments, the second nucleic acid construct of the invention can comprises a second selectable marker, SM2, which is a nucleotide sequence, the expression of which results in a nutritional deficiency. Thus, in some embodiments, the second selectable marker, SM2, is a nucleotide sequence, the expression of which results in a plant having a uracil deficiency, a histidine deficiency, a leucine deficiency and any combination thereof, as well as any other nutritional deficiency now known or later identified.

Furthermore, as used herein the phrase "reduced or no sexual reproduction" refers to an inability or a reduced ability of a plant to reproduce sexually. Reduced or no sexual reproduction can also be referred to as "total vegetative growth," which describes plants that do not enter the reproductive growth stage, and in some examples describes plants having a significant delay in flowering, such as a delay of at least one month, at least two months, at least three months, or even at least six months or longer. Such an attribute of no or reduced ability to reproduce sexually in a transgenic plant allows for the prevention or reduction of transgene flow from the transgenic plant to a non-transgenic plant.

In plants, gene flow can occur through movement of, for example, pollen grains and seeds in the environment. Various gene containment strategies have been developed to alter gene flow by interfering with flower pollination, fertilization, or fruit development (Daniell, *Nature Biotechnol.* 20:581-586 (2002)). Interference with the development of male reproductive structures through genetic engineering has been widely used as an effective strategy for the development of male sterility in plants. Selective ablation of tapetal cells has been carried out by cell-specific expression of cytotoxic molecules (Moffatt et al., *Plant Physiol.* 86:1150-1154 (1988); Mariani et al., *Nature* 347:737-741 (1990); Tsuchiya et al., *Plant Cell Physiol.* 36:487-494 (1995); De Block et al., *Theor. Appl. Genet.* 95:125-131 (1997); Jagannath et al., *Mol. Breed.* 8:11-23 (2001)) or by the introduction of an antisense gene essential for pollen development, which blocks pollen development, giving rise to male sterility (Xu et al. *Proc. Nat. Acad. Sci.* 92:2106-2110 (1995); Luo et al., *Plant J.* 23:423-430 (2000); Goetz et al., *Proc. Nat. Acad. Sci.* 98:6522-6523 (2001)).

The present invention provides a method of reducing or eliminating sexual reproduction in a transgenic plant. In exemplary embodiments of the invention, a hybrid transgenic plant is produced that is stably transformed with a nucleic acid construct comprising at least one nucleotide sequence, the expression of which results in no or reduced sexual reproduction, NSRS. Such nucleotide sequences include, but are not limited to, nucleotide sequences that modulate the reproductive transition from a vegetative meristem or flower promotion gene or coding sequence, or flower repressor gene or coding sequence. In the case of a flower promotion gene or coding sequence, antisense or RNAi nucleic acid molecules specific for the flower promotion gene or coding sequence could be used to down-regulate expression of the gene. As used herein "down-regulation" refers to any process that results in decreased production of a gene product. A gene product can be RNA (such as mRNA, rRNA, tRNA, and structural RNA) or protein. Therefore, down-regulation of a gene or coding sequence includes processes that decrease transcription of a gene or translation of mRNA. Down regulation does not require a 100% decrease in gene expression but instead can include a decrease of about 5%, about 10%, about 20%, about 30%, about 40%, about 50%, about 60%, about 70%, about 75%, about 85%, about 90%, about 95%, or about 99%, for example, as compared to the amount of gene expression observed in a non-transgenic plant of the same variety as the transgenic plant.

Alternatively, up-regulation of a flower repressor gene or coding sequence transformed into the transgenic plant can be used to reduce or eliminate sexual reproduction in a transgenic plant. As used herein "up-regulation" of a gene or coding sequence refers to any process that results in an increased production of a gene product or product encoded by the coding sequence, such as RNA (such as mRNA, rRNA, tRNA, and structural RNA) or protein. Thus, up-regulation of a gene or coding sequence includes any process that increases transcription of a gene or coding sequence or translation of mRNA.

For example, a flower repressor coding sequence in a plant can be upregulated or over-expressed by operably linking the repressor coding sequence (or fragment or variant thereof that retains at least 50% of the biological activity of the native sequence) to a constitutive or an inducible promoter. In some examples, up-regulation includes increases of about 5%, about 10%, about 20%, about 30%, about 40%, about 50%, about 60%, about 70%, about 75%, about 85%, about 90%, about 95%, about 99%, or about 100%, for example as compared to the amount of expression observed in a non-transgenic plant of the same variety as the transgenic plant.

Three growth phases are generally observed in the life cycle of a flowering plant: vegetative, inflorescence and floral. The switch from vegetative to reproductive or floral growth requires a change in the developmental program of the descendents of the stem cells in the shoot apical meristem. In the vegetative phase, the shoot apical meristem generates leaves that provide resources necessary to produce fertile offspring. Upon receiving the appropriate environmental and developmental signals, the plant switches to floral (reproductive) growth and the shoot apical meristem enters the inflorescence phase, giving rise to an inflorescence with flower primordia. During this phase, the fate of the shoot apical meristem and the secondary shoots that arise in the axils of the leaves is determined by a set of meristem identity genes, some of which prevent and some of which promote the development of floral meristems. Once established, the plant enters the late inflorescence phase where the floral organs are produced. Two basic types of inflorescences have been identified in plants: determinate and indeterminate. In a species producing a determinate inflorescence, the shoot apical meristem eventually produces floral organs and the production of meristems is terminated with a flower. In those species producing an indeterminate inflorescence, the shoot apical meristem is not converted to a floral identity and therefore only produces floral meristems from its periphery, resulting in a continuous growth pattern.

In dicots, after the transition from vegetative to reproductive development, floral meristems are initiated by the action of a set of genes called floral meristem identity genes. FLORICAULA (flo) of *Antirrhinum* and its *Arabidopsis* counterpart, LEAFY (lfy), are floral meristem identity genes that participate in the reproductive transition to establish floral fate. In strong flo and lfy mutant plants, flowers are transformed into inflorescence shoots (Coen et al., *Cell* 63:1311-1322 (1990); Weigel et al. *Cell* 69:843-859, (1992)), indicating that flo and lfy are exemplary flower-promotion genes.

In monocots, FLO/LFY homologs have been identified in several species, such as rice (Kyozuka et al., *Proc. Natl. Acad. Sci.* 95:1979-1982 (1998)); *Lolium temulentum*, maize, and ryegrass (*Lolium perenne*). The FLO/LFY homologs from different species have high amino acid sequence homology and are well conserved in the C-terminal regions (Kyozuka et al., *Proc. Natl. Acad. Sci.* 95:1979-1982 (1998); Bomblies et al., *Development* 130:2385-2395 (2003)).

In addition to flo/lfy genes or coding sequences, other examples of flower promotion genes or coding sequences include, but are not limited to, APETALA1 (Accession no.

NM105581)/SQUAMOSA (apl/squa) in *Arabidopsis* and *Antirrhinum*, CAULIFLOWER (cal, Accession no. AY174609), FRUITFUL (ful, Accession no. AY173056), FLOWERING LOCUS T (Accession no. AB027505), and SUPPRESSOR OF OVEREXPRESSION OF CONSTANS1 (soc1) in *Arabidopsis* (Samach et al., *Science* 288:1613-1616 (2000); Simpson and Dean, *Science* 296:285-289 (2002)); Zik et al., *Annu. Rev. Cell Dev. Biol.* 19:119-140 (2003)).

Additional flowering related genes or coding sequences of the present invention include, but are not limited to, TERMINAL FLOWER 1 (tlf1) in *Arabidopsis* and its homolog CENTRORADIALS (cen) in *Antirrhinum*; FLOWERING LOCUS C (flc) and the emf gene in *Arabidopsis*. It is noted that any flower-promotion or flower-related coding sequence(s), the down-regulation of which results in no or reduced sexual reproduction (or total vegetative growth), can be used in the present invention.

Down-regulation of expression of one or more flower promotion or coding sequences in a plant, such as a flo/lfy homolog, results in reduced or no sexual reproduction or total vegetative growth in the transgenic plant, whereby the transgenic plant is unable to produce flowers (or there is a significant delay in flower production). The high conservation observed among flo/lfy homologs indicates that further flo/lfy homologs can be isolated from other plant species by using, for example, the methods of Kyozuka et al. (*Proc. Natl. Acad. Sci.* 95:1979-1982 (1998)) and Bomblies et al. (*Development* 130:2385-2395 (2003)). For example, the flo/lfy homolog from bentgrass (*Agrostis stolonifera* L.) has been cloned (U.S. Patent Application No. 2005/0235379).

A transgenic plant expressing reduced or no sexual reproduction can reduce transgene escape by about 5%, about 10%, about 20%, about 30%, about 40%, about 50%, about 60%, about 70%, about 75%, about 80%, about 85%, about 90%, about 95%, about 99% or about 100%, as compared to, for example, a transgenic plant not down-regulated for expression of one or more flower promotion genes. Any method known in the art can be used to reduce or down-regulate expression of, e.g., a flo/lfy homolog or other flower promotion gene or coding sequence in a plant. In particular examples, antisense, antigene and/or RNAi approaches can be used, as are well known in the art.

In particular examples, down-regulation of expression of a flower promotion gene does not require a 100% reduction in such expression. For example, a reduction of about 5%, about 10%, about 20%, about 30%, about 40%, about 50%, about 60%, about 70%, about 75%, about 85%, about 90%, about 95%, about 99% as compared to expression of the gene in a non-transgenic plant of the same species, indicates that expression of the gene was down regulated. In some embodiments, down-regulation reduces expression by 100%, such that expression of the gene is not detectable according to standard methods known in the art for detection of gene expression.

In further embodiments of the present invention, expression of one or more flower-repressor genes can be up-regulated using methods known in the art. Flower repressor genes or coding sequences can disrupt the vegetative phase transition or alter meristem identity. Particular examples of such genes or coding sequences include, but are not limited to, TERMINAL FLOWER 1 (tfl1, Accession no. NM120465) in *Arabidopsis* and its homolog CENTRORADIALS (cen) in *Antirrhinum* (Bradley et al. *Nature* 376:791-797 (1996)), FLOWERING LOCUS C (flc, Accession no. AY769360) and emf (Sung et al., *Science* 258:1645-1647 (1992)) in *Arabidopsis*, and any combination thereof. Any flower-repressor gene or coding sequence, the expression of which results in no or reduced sexual reproduction (or total vegetative growth), can be used in the present invention.

Increased expression of a flower-repressor gene or coding sequence can result in a delay or suppression of flowering (vegetative growth) of the transgenic plant, thus decreasing transgene escape. Similar to the down-regulation of flower promoting genes, transgenic plants having increased expression of a flower-repressor gene or coding sequence can reduce transgene escape by about 5%, about 10%, about 20%, about 30%, about 40%, about 50%, about 60%, about 70%, about 75%, about 80%, about 85%, about 90%, about 95%, or about 100%, as compared to, for example, a transgenic plant not up-regulated for expression of one or more flower repressor genes.

Other nucleotide sequences, the expression of which affects the ability of a plant to reproduce sexually, can include nucleotide sequences encoding cytotoxic polypeptides. Nucleotide sequences encoding cytotoxic polypeptides useful in the present invention include, but are not limited to, a ribonuclease, as well as any other nucleotide sequence encoding a cytotoxic polypeptide now known or later identified. Ribonucleases useful in the present invention include, but are not limited to, barnase, and any other ribonuclease now known or later identified that can act as a cytotoxic polypeptide.

Accordingly, in some embodiments of the present invention a method is provided wherein the first nucleic acid construct comprises at least one nucleotide sequence, the expression of which results in no or reduced sexual reproduction, NRSR, which can be, for example, a nucleotide sequence encoding barnase, an antisense sequence of a pollen- and tapetum-specific nucleotide sequence, an RNAi (e.g., of FLORICAULA/LEAFY), an antisense sequence (e.g., of FLORICAULA/LEAFY), and any combination thereof. In additional embodiments of the invention, the first nucleic acid construct can comprises more than one NRSR.

It is noted that in certain embodiments of the present invention, the NRSR can be a reporter or marker sequence. Reporter and marker sequences are well known in the art, for example, those described above.

The present invention further provides a method of producing a hybrid transgenic plant comprising a nucleic acid construct comprising at least one nucleotide sequence of interest, NOI. NOIs can be any nucleotide sequence, the expression of which results in a phenotype of interest, particularly a phenotype that imparts an agronomically or horticulturally important trait to the transgenic plant.

Thus, in some embodiments of the present invention, the NOI can be a nucleotide sequence, the expression of which results in a phenotype including, but not limited to, herbicide resistance or tolerance, drought tolerance, salt tolerance, cold tolerance, pigmentation, enhanced seed production, increased root growth, increased vegetative growth, enhanced seed production, enhanced phosphate uptake, phytoremediation, disease resistance, insect resistance, wear tolerance (high traffic tolerance), early flowering, shade tolerance, hypoxia tolerance, fungal resistance, stay-green, delayed senescence, decreased nitrogen, endophyte-enhanced, increased biomass production, increased yield, nutrient content, and any combination thereof, as well as any other agronomically or horticulturally desirable phenotypic trait now known or later identified.

Nonlimiting examples of an NOI of this invention include, but are not limited to, nucleotide sequences, the expression of which results in resistance or tolerance to bialaphos, glyphosate, sulfonylurea, glufosinate ammonium, bromoxynil and/or 2,4-dichlorophenoxyacetate.

An NOI of this invention can also be nucleotide sequences that produce disease and/or insect resistance, as are well known in the art including, but not limited to, the Bt gene or coding sequence, the antimicrobial peptide genes or coding sequences (amp) (Asiegbo et al., *FEMS Microbiol. Lett.* 228: 27-31 (2003), and those described by Dickerman et al. (*Plant and Animal Genome Conference*, San Diego, Calif., January 17-21, (1999)), Ayliffe et al. (*Ann. Bot.* 94:765-773 (2004)); McDowell et al. (*Trends in Biotechnol.* 21:178-183 (2003)) and Singh et al. (*Disease and Insect Resistance in Plants*, Science Publishers (USA), 417 pp. (2005)).

Examples of an NOI of this invention that produce a phenotype of drought tolerance, cold tolerance or salt tolerance are known in the art and include, but are not limited to, a nucleotide sequence encoding the *Arabidopsis* vacuolar H$^+$-pyrophosphatase gene or coding sequence, AVP1, and those described by Iuchi et al. (*Plant J.* 27(4):325-332 (2001)); Umezawa et al. (*Curr Opin Biotechnol.* 17(2):113-22 (2006)); U.S. Pat. No. 5,837,545; Oraby et al. (*Crop Sci.* 45:2218-2227 (2005)) and Shi et al. (*Proc. Natl. Acad. Sci.* 97:6896-6901 (2000)).

Examples of stay-green genes are describe in United States Patent 2007/0094744 and by Borrell et al. (*Proceedings of the 4th International Crop Science Congress*, Brisbane, Australia, Sep. 26-Oct. 1 (2004)).

Furthermore, in certain embodiments of the present invention, an NOI can be a reporter or marker coding sequence. Reporter and marker genes and coding sequences are well known in the art, for example, those described above.

A further embodiment of the invention provides a method of producing a transgenic hybrid plant having no or reduced sexual reproduction, comprising: (a) stably transforming a first plant with a first nucleic acid construct comprising: (i) a promoter, P1, wherein P1 is a rice ubiquitin promoter; (ii) a site specific recombinase, RS1, wherein RS1 is Cre; (iii) a promoter, P2, wherein P2 is a 35S promoter; (iv) a selectable marker, SM1, wherein SM1 is hyg; (v) a promoter P3, wherein P3 is the soybean heat shock promoter, Gmhsp 17.5-E; (vi) at least one nucleotide sequence the expression of which results in no or reduced sexual reproduction, NRSR, wherein NRSR is an RNAi and/or an antisense sequence of flo/lfy; and (vii) at least two target sites, TRS2, specific for a site specific recombinase, RS2, that is different from the first site specific recombinase, RS1, wherein RS2 is FLP and TRS2 is FRT, and further wherein P1 is operably located upstream of RS1, P2 is operably located upstream of SM1, P3 is operably located upstream of NRSR, a first TRS2 is located immediately downstream of P1 and a second TRS2 is located upstream of NRSR; (b) stably transforming a second plant with a second nucleic acid construct comprising: (i) a promoter, P4, wherein P4 is a rice ubiquitin promoter; (ii) a site specific recombinase, RS2, that is different from the site specific recombinase, RS1, of (a), wherein RS1 is Cre and RS2 is FLP; (iii) a selectable marker, SM2, wherein SM2 is bar; (iv) at least one nucleotide sequence of interest, NOT; (v) at least two target sites, TRS1, specific for the site specific recombinase, RS1, wherein RS1 is Cre and TRS1 is lox; and (vi) at least two target sites, TRS2, specific for the site specific recombinase, RS2, wherein RS2 is FLP and TRS2 is FRT, and further wherein P4 is operably located upstream of SM2, RS2 is located downstream of SM2, a first TRS1 is located immediately downstream of P4, a second TRS1 is located immediately downstream of SM2, a first TRS2 is located immediately upstream of RS2 and downstream of the second TRS1, a second TRS2 is located immediately downstream of RS2 and the NOT is located immediately downstream of the second TRS2; and (c) cross-pollinating the stably transformed first plant of (a) with the stably transformed second plant of (b) to produce a transgenic hybrid plant having no or reduced sexual reproduction.

An additional embodiment of the invention provides a method of producing a transgenic hybrid plant having no or reduced sexual reproduction, the method comprising: (a) stably transforming a first plant with a first nucleic acid construct comprising: (i) a promoter, P1, wherein P1 is a rice ubiquitin promoter; (ii) a site specific recombinase, RS1, wherein RS1 is Cre; (iii) a promoter, P2, wherein P2 is a 35S promoter; (iv) a selectable marker, SM1, wherein SM1 is hyg; (v) a promoter P3, wherein P3 is the soybean heat shock promoter, Gmhsp 17.5-E; (vi) at least one nucleotide sequence the expression of which results in no or reduced sexual reproduction, NRSR, wherein NSRS is a nucleotide sequence encoding the polypeptide barnase; and (vii) at least two target sites, TRS2, specific for a site specific recombinase, RS2, that is different from the first site specific recombinase, RS1, wherein RS2 is FLP and TRS2 is FRT, and further wherein P1 is operably located upstream of RS1, P2 is operably located upstream of SM1, P3 is operably located upstream of NRSR, a first TRS2 is located immediately downstream of P1 and a second TRS2 is located upstream of NRSR; (b) stably transforming a second plant with a second nucleic acid construct comprising: (i) a promoter, P4, wherein P4 is a rice ubiquitin promoter; (ii) a site specific recombinase, RS2, that is different from the site specific recombinase, RS1, of (a), wherein RS1 is Cre and RS2 is FLP; (iii) a selectable marker, SM2, wherein SM2 is bar; (iv) at least one nucleotide sequence of interest, NOI; (v) at least two target sites, TRS1, specific for the site specific recombinase, RS1, wherein RS1 is Cre and TRS1 is lox; and (vi) at least two target sites, TRS2, specific for the site specific recombinase, RS2, wherein RS2 is FLP and TRS2 is FRT, further wherein P4 is operably located upstream of SM2, RS2 is located downstream of SM2, a first TRS1 is located immediately downstream of P4, a second TRS1 is located immediately downstream of SM2, a first TRS2 is located immediately upstream of RS2 and downstream of the second TRS1, a second TRS2 is located immediately downstream of RS2 and the NOI is located immediately downstream of the second TRS2; and (c) cross-pollinating the stably transformed first plant of (a) with the stably transformed second plant of (b) to produce a transgenic hybrid plant having no or reduced sexual reproduction.

A further embodiment of the invention provides a method of producing a transgenic hybrid plant having no or reduced sexual reproduction, the method comprising: (a) stably transforming a first plant with a first nucleic acid construct comprising: (i) a promoter, P1, wherein P1 is a rice ubiquitin promoter; (ii) a site specific recombinase, RS1, wherein RS1 is Cre; (iii) a promoter, P2, wherein P2 is a 35S promoter; (iv) a selectable marker, SM1, wherein SM1 is hyg; (v) a promoter P3, wherein P3 is the soybean heat shock promoter, Gmhsp 17.5-E; (vi) at least one nucleotide sequence the expression of which results in no or reduced sexual reproduction, NRSR, wherein NRSR is an RNAi and/or an antisense sequence of a pollen- and tapetum-specific nucleotide sequence; and (vii) at least two target sites, TRS2, specific for a site specific recombinase, RS2, that is different from the site specific recombinase, RS1, wherein RS2 is FLP and TRS2 is FRT, and further wherein P1 is operably located upstream of RS1, P2 is operably located upstream of SM1, P3 is operably located upstream of NRSR, a first TRS2 is located immediately downstream of P1 and a second TRS2 is located upstream of NRSR; (b) stably transforming a second plant with a second nucleic acid construct comprising: (i) a promoter, P4, wherein P4 is a rice ubiquitin promoter; (ii) a site specific recombinase, RS2, that is different from the site specific recombinase, RS1, of (a), wherein RS1 is Cre and RS2 is FLP; (iii) a selectable marker, SM2, wherein SM2 is bar; (iv) at least one nucleotide sequence of interest, NOI; (v) at least two target sites, TRS1, specific for the site specific recombinase, RS1, wherein RS1 is Cre and TRS1 is lox; and (vi) at least two target sites, TRS2, specific for the site specific recombinase, RS2, wherein RS2 is FLP and TRS2 is FRT, further wherein P4 is operably located upstream of SM2, RS2 is located downstream of SM2, a first TRS1 is located immediately downstream of P4, a second TRS1 is located immediately downstream of SM2, a first TRS2 is located immediately upstream of RS2 and downstream of the second TRS1, a second TRS2 is located immediately downstream of RS2 and the NOI is located immediately downstream of the second TRS2; and (c) cross-pollinating the stably transformed first plant of (a) with the stably transformed second plant of (b) to produce a transgenic hybrid plant having no or reduced sexual reproduction.

A further aspect of the present invention is a transgenic hybrid plant comprising: (a) a first nucleic acid construct comprising: (i) a promoter, P1; (ii) a target site, TRS2, specific for a site specific recombinase, RS2; and (iii) at least one nucleotide sequence the expression of which results in no or reduced sexual reproduction, NRSR, and wherein P1 is upstream of and operably associated with NRSR, and the target site, TRS2, is immediately downstream of P1; and (b) a second nucleic acid construct comprising: (i) a promoter, P4; (ii) a target site, TRS2, specific for the site specific recombinase, RS2; (iii) a target site, TRS1, specific for a site specific recombinase, RS1; and (iv) at least one nucleotide sequence of interest, NOI, and wherein P4 is upstream of and operably associated with the NOI, and the target site, TRS1, is immediately downstream of P4 and the NOI is immediately downstream of TRS2.

The present invention further provides a transgenic hybrid plant comprising: (a) a first nucleic acid construct comprising: (i) a promoter, P1, wherein P1 is a rice ubiquitin promoter; (ii) a target site, TRS2, specific for a site specific recombinase, RS2, wherein TRS2 sequence is FRT; and (iii) at least one nucleotide sequence the expression of which results in no or reduced sexual reproduction, NRSR, wherein NSRS is an RNAi and/or an antisense sequence of flo/lfy, and wherein P1 is upstream of and operably associated with NRSR, and the target site, TRS2, is immediately downstream of P1; and (b) a second nucleic acid construct comprising: (i) a promoter, P4, wherein P4 is a rice ubiquitin promoter; (ii) a target site, TRS2, specific for the site specific recombinase, RS2, wherein TRS2 is FRT; (iii) a target site, TRS1, specific for a site specific recombinase, RS1, wherein TRS1 is loxP; and (iv) at least one nucleotide sequence of interest, NOI, and wherein P4 is upstream of and operably associated with the NOI, and the target site, TRS1, is immediately downstream of P4 and the NOI is immediately downstream of TRS2.

The present invention additionally provides a transgenic hybrid plant comprising: (a) a first nucleic acid construct comprising: (i) a promoter, P1, wherein P1 is a rice ubiquitin promoter; (ii) a target site, TRS2, specific for a site specific recombinase, RS2, wherein TRS2 sequence is FRT; and (iii) at least one nucleotide sequence the expression of which results in no or reduced sexual reproduction, NRSR, wherein NSRS is nucleotide sequence encoding barnase, and wherein P1 is upstream of and operably associated with NRSR, and the target site, TRS2, is immediately downstream of P1; and (b) a second nucleic acid construct comprising: (i) a promoter, P4, wherein P4 is a rice ubiquitin promoter; (ii) a target site, TRS2, specific for the site specific recombinase, RS2, wherein TRS2 is FRT; (iii) a target site, TRS1, specific for a site specific recombinase, RS1, wherein TRS1 is loxP; and (iv) at least one nucleotide sequence of interest, NOI, and wherein P4 is upstream of and operably associated with the NOI, and the target site, TRS1, is immediately downstream of P4 and the NOI is immediately downstream of TRS2.

The present invention further provides a transgenic hybrid plant comprising: (a) a first nucleic acid construct comprising: (i) a promoter, P1, wherein P1 is a rice ubiquitin promoter; (ii) a target site, TRS2, specific for a site specific recombinase, RS2, wherein TRS2 sequence is FRT; and (iii) at least one nucleotide sequence the expression of which results in no or reduced sexual reproduction, NRSR, wherein NSRS is an RNAi and/or an antisense sequence of a pollen- and tapetum-specific nucleotide sequence, and wherein P1 is upstream of and operably associated with NRSR, and the target site, TRS2, is immediately downstream of P1; and (b) a second nucleic acid construct comprising: (i) a promoter, P4, wherein P4 is a rice ubiquitin promoter; (ii) a target site, TRS2, specific for the site specific recombinase, RS2, wherein TRS2 is FRT; (iii) a target site, TRS1, specific for a site specific recombinase, RS1, wherein TRS1 is loxP; and (iv) at least one nucleotide sequence of interest, NOI, and wherein P4 is upstream of and operably associated with the NOI, and the target site, TRS1, is immediately downstream of P4 and the NOI is immediately downstream of TRS2

A still further aspect of the invention is a method of reducing transgene flow to non-transgenic plants comprising planting a field with a plurality of plants comprising, consisting essentially of and/or consisting of a hybrid transgenic plant of the present invention.

Another embodiment of present invention provides a nucleic acid construct comprising: (a) a promoter, P1; (b) a site specific recombinase, RS1; (c) a promoter, P2; (d) a first selectable marker, SM1; (e) a promoter P3; (f) at least one nucleotide sequence the expression of which results in no or reduced sexual reproduction, NRSR; and (g) at least two target sites, TRS2, specific for a site specific recombinase, RS2, wherein RS2 is different from the site specific recombinase, RS1, of (b) above, and further wherein P1 is located upstream of and operably associated with RS1, P2 is located upstream of and operably associated with SM1, P3 is located upstream of and operably associated with NRSR, a first TRS2 is located immediately downstream of P1 and a second TRS2 is located upstream of NRSR.

In other embodiments of present invention, a nucleic acid construct is provided, the nucleic acid construct comprising: (a) a promoter, P1, wherein P1 is a rice ubiquitin promoter; (b) a site specific recombinase, RS1, wherein RS1 is Cre; (c) a promoter, P2, wherein P2 is a 35S promoter; (d) a selectable marker, SM1, wherein SM1 is hyg; (e) a promoter, P3, wherein P3 is the soybean heat shock promoter Gmhsp 17.5-E; (f) at least one nucleotide sequence the expression of which results in no or reduced sexual reproduction, NRSR, wherein NSRS is an RNAi and/or an antisense sequence of flo/lfy; and (g) at least two target sites, TRS2, specific for a site specific recombinase, RS2, wherein RS2 is different from the site specific recombinase, RS1, of (b) above, further wherein TRS2 is FRT, and still further wherein P1 is located upstream of and operably associated with RS1, P2 is located upstream of and operably associated with SM1, P3 is located upstream of and operably associated with NRSR, a first TRS2 is located immediately downstream of P1 and a second TRS2 is located upstream of NRSR.

In other embodiments of the present invention, a nucleic acid construct is provided, the nucleic acid construct comprising: (a) a promoter, P1, wherein P1 is a rice ubiquitin promoter; (b) a site specific recombinase, RS1, wherein RS1 is Cre; (c) a promoter, P2, wherein P2 is a 35S promoter; (d) a selectable marker, SM1, wherein SM1 is hyg; (e) a promoter, P3, wherein P3 is the soybean heat shock promoter Gmhsp 17.5-E; (f) at least one nucleotide sequence, the expression of which results in no or reduced sexual reproduction, NRSR, wherein NSRS is a nucleotide sequence encoding the peptide barnase; and (g) at least two target sites, TRS2, specific for a site specific recombinase, RS2, wherein RS2 is different from the site specific recombinase, RS1, of (b) above, further wherein TRS2 is FRT, and further wherein P1 is located upstream of and operably associated with RS1, P2 is located upstream of and operably associated with SM1, P3 is located upstream of and operably associated with NRSR, a first TRS2 is located immediately downstream of P1 and a second TRS2 is located upstream of NRSR.

In some embodiments of the present invention, a nucleic acid construct is provided, the nucleic acid construct comprising: (a) a promoter, P1, wherein P1 is a rice ubiquitin promoter; (b) a site specific recombinase, RS1, wherein RS1 is Cre; (c) a promoter, P2, wherein P2 is a 35S promoter; (d) a selectable marker, SM1, wherein SM1 is hyg; (e) a promoter, P3, wherein P3 is the soybean heat shock promoter Gmhsp 17.5-E; (f) at least one nucleotide sequence, the expression of which results in no or reduced sexual reproduction, NRSR, wherein NSRS is an RNAi and/or an antisense sequence of a pollen- and tapetum-specific nucleotide sequence; and (g) at least two target sites, TRS2, specific for a site specific recombinase, RS2, wherein RS2 is different from the site specific recombinase, RS1, of (b) above, further wherein TRS2 is FRT, and further wherein P1 is located upstream of and operably associated with RS1, P2 is located upstream of and operably associated with SM1, P3 is located upstream of and operably associated with NRSR, a first TRS2 is located immediately downstream of P1 and a second TRS2 is located upstream of NRSR.

In some embodiments of the invention, a nucleic acid construct is provided, the nucleic acid construct comprising in the 5' to 3' direction (a) a promoter, P1; (b) a target site, TRS2, specific for a site specific recombinase, RS2, wherein RS2 is different from a site specific recombinase, RS1, (c) a site specific recombinase, RS1; (d) a promoter, P2; (e) a selectable marker, SM1; (f) a promoter P3; (g) a target site, TRS2, specific for a site specific recombinase, RS2, wherein RS2 is different from the site specific recombinase, RS1; (h) at least one nucleotide sequence the expression of which results in no or reduced sexual reproduction, NRSR; and, and further wherein P1 is operably associated with RS1, P2 operably associated with SM1, and P3 operably associated with NRSR.

In other embodiments of the invention, a nucleic acid construct is provided, the nucleic acid construct comprising in the 5' to 3' direction (a) a promoter, P1, wherein P1 is a rice ubiquitin promoter; (b) a target site, TRS2, specific for a site specific recombinase, RS2, wherein RS2 is different from a site specific recombinase, RS1, further wherein TRS2 is FRT (c) a site specific recombinase, RS1, wherein RS1 is Cre; (d) a promoter, P2, wherein P2 is a $^{35}$S promoter; (e) a selectable marker, SM1, wherein SM1 is hyg; (f) a promoter P3, wherein P3 is the soybean heat shock promoter Gmhsp 17.5-E; (g) a target site, TRS2, specific for a site specific recombinase, RS2, wherein RS2 is different from the site specific recombinase, RS1, further wherein TRS2 is FRT; (h) at least one nucleotide sequence the expression of which results in no or reduced sexual reproduction, NRSR; and, and further wherein P1 is operably associated with RS1, P2 operably associated with SM1, and P3 operably associated with NRSR.

In another embodiment a nucleic acid construct is provided, the nucleic acid construct comprising (a) a promoter, P4; (b) a selectable marker, SM2; (c) a site specific recombinase, RS2; (d) at least two target sites, TRS2, specific for the site specific recombinase, RS2; (e) at least two target sites, TRS1, specific for a site specific recombinase, RS1, that is different from the site specific recombinase, RS2, of (c) above; (f) at least one nucleotide sequence of interest, NOI; and further wherein P4 is located upstream of and operably associated with SM2, RS2 is located downstream of SM2, a first TRS1 is located immediately downstream of P4, a second TRS1 is located immediately downstream of SM2, a first TRS2 is located immediately upstream of RS2 and downstream of the second TRS1, a second TRS2 is located immediately downstream of RS2 and the NOI is located immediately downstream of the second TRS2.

Additionally provided is a nucleic acid construct comprising: (a) a promoter, P4, wherein P4 is a rice ubiquitin promoter; (b) a selectable marker, SM2, wherein SM2 is bar; (c) a site specific recombinase, RS2, wherein RS2 is FLP; (d) at least two target sites, TRS2, specific for the site specific recombinase, RS2, wherein TRS2 is FRT; (e) at least two target sites, TRS1, for a site specific recombinase, RS1 that is different from the site specific recombinase, RS2, of (c) above, wherein TRS1 is lox; and (f) at least one nucleotide sequence of interest, NOT; and further wherein P4 is located upstream of and operably associated with SM2, RS2 is located downstream of SM2, a first TRS1 is located immediately downstream of P4, a second TRS2 is located immediately downstream of SM2, a first TRS2 is located immediately upstream of RS2 and downstream of the second TRS1, a second TRS2 is located immediately downstream of RS2 and the NOT is located immediately downstream of the second TRS2.

In other embodiments, a nucleic acid construct is provided comprising in the 5' to 3' direction: (a) a promoter, P4; (b) a target site, TRS1, specific for a site specific recombinase, RS1 that is different from a site specific recombinase, RS2; (c) a selectable marker, SM2; (d) a target site, TRS1, specific for the site specific recombinase, RS1; (e) a target site, TRS2, specific for the site specific recombinase, RS2; (f) a site specific recombinase, RS2; (g) a target site, TRS2, specific for the site specific recombinase, RS2; and (h) at least one nucleotide sequence of interest, NOT; and further wherein P4 is operably associated with SM2.

In further embodiments, a nucleic acid construct is provided, the nucleic acid construct comprising in the 5' to 3' direction: (a) a promoter, P4, wherein P4 is a rice ubiquitin promoter; (b) a target site, TRS1, specific for a site specific recombinase, RS1 that is different from a site specific recombinase, RS1, wherein TRS1 is lox; (c) a selectable marker, SM2, wherein SM2 is bar; (d) a target site, TRS1, specific for the site specific recombinase, RS1, wherein TRS1 is lox; (e) a target site, TRS2, specific for the site specific recombinase, RS2, wherein TRS2 is FRT; (f) a site specific recombinase, RS2, wherein RS2 is FLP; (g) a target site, TRS2, specific for the site specific recombinase, RS2, wherein TRS2 is FRT; and (h) at least one nucleotide sequence of interest, NOI; and further wherein P4 is operably associated with SM1.

A further embodiment of the present invention is a transgenic plant comprising one or more heterologous nucleic acid constructs of the present invention in any combination.

A still further embodiment is a transgenic pollen grain of a transgenic plant of the present invention.

Also provided is a transgenic ovule of a transgenic plant of the present invention.

Additionally provided is a tissue culture of regenerable transgenic cells of a transgenic plant of the present invention.

Further provided is a transgenic seed of a plant of the present invention, wherein the transgenic seed comprises a heterologous nucleic acid construct of the present invention.

EXAMPLES

Example 1

Figure 2:
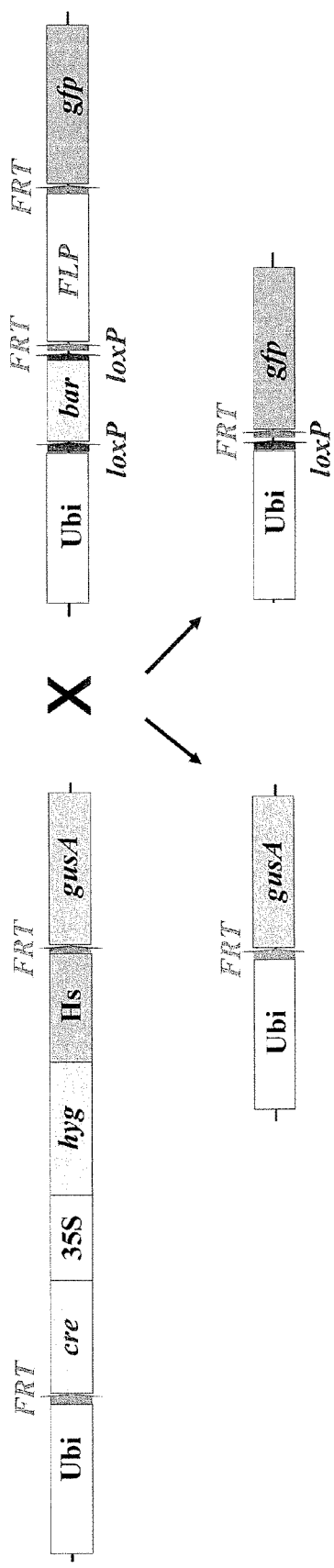
FIG. 2 shows two exemplary nucleic acid constructs of the present invention useful in the production of transgenic plant lines.

The present example is provided to demonstrate the use of a dual site-specific recombination system such as that described herein. In this example the site-specific recombinases for eliminating unwanted transgenes are FLP/FRT and Cre/lox. This, in combination with controllable total sterility technology (i.e., total vegetative growth or no or reduced sexual reproduction), will produce environmentally safe, clean transgenic turfgrass plants. As illustrated in FIG. 2, two transgenic lines are produced. The first line will contain a Cre-expressing construct, pSBUbi-FRT-Cre-35S/hyg-Hs-FRT-gusA, in which the recombinase Cre-coding sequence is linked to a CaMV35S promoter-driving the marker gene, hyg and followed by the soybean heat-shock promoter, Hs, which is flanked by directly oriented FLP recombinase target sites, FRTs. This FRT-flanked cassette serves to separate a rice Ubi promoter from a reporter gene gusA (in other exemplary embodiments, an RNAi construct or an antisense sequence of the flower-specific gene, flo/lfy homolog, and/or a cytotoxic gene, such as barnase, can be used). Since, in this construct, the GUS coding sequence has an inducible promoter only, this transgenic line should not express GUS.

The other transgenic line will harbor a FLP-containing construct, pSBUbi-loxP-bar-loxP-FRT-FLP-FRT-gfp, in which the recombinase Cre target site loxP-flanked marker gene, bar, is linked to the FLP recombinase target site FRT-flanked recombinase FLP-coding sequence. This whole cassette serves to separate a rice Ubi promoter from a reporter gene, gfp (in other embodiments the nucleotide sequence of interest (NOI) can be any nucleotide sequence the expression of which results in a phenotype imparting a desired agricultural and or horticultural trait as described herein). Since, in this construct, the reporter gene (or its coding sequence), gfp, has no operably linked promoter sequence, this transgenic line should not express GFP.

When the two transgenic lines are cross-pollinated, the Cre recombinase in the hybrid will cause excision of the loxP-flanked blocking fragment (bar gene or coding sequence). This in turn will bring into proximity an upstream Ubi promoter and a downstream FRT-flanked FLP-coding sequence, resulting in the expression of FLP and consequently self-excision of the FLP-coding sequence. This will bring together the upstream rice Ubi promoter and the downstream reporter gene, gfp, resulting in GFP expression (or the expression of a NOI in other embodiments). The expression of FLP will also cause the excision of the FRT-flanked Cre recombinase gene as well as its linked marker gene, hyg and the heat-shock promoter, Hs, bringing together an upstream rice Ubi promoter and a downstream reporter gene, gusA, resulting in GUS expression in the hybrids. In case of incomplete DNA recombination, the induced activation of heat-shock promoter Hs (in other embodiments, promoters responsive to other environmental stimuli, or synthetic compounds or developmental and cell-specific factors can be used) will lead to GUS expression (or reduced or no sexual reproduction in embodiments in which the NSRS is a nucleotide sequence the expression of which is reduced or no sexual reproduction). This provides a contingency plan should low recombinase-mediated excision efficiency occur.

Example 2

Two constructs are prepared for delivery into creeping bentgrass using *Agrobacterium*-mediated plant transformation, creating transgenic lines harboring FLP-containing or Cre-containing constructs, respectively. Using pSB11-based binary vectors (Komari et al., 1996) for the construction, a reliable *Agrobacterium*-mediated turfgrass transformation procedure is established that enables routine production of transgenic turfgrass plants (Luo et al., 2004a; b; 2005).

Example 3

Production of Constructs, pSBUbi-FRT-Cre-35S/ hyg-Hs-FRT-gusA, and pSBUbi-loxP-bar-loxP-FRT-FLP-FRT-gfp Two pSB11-based *Agrobacterium* binary vectors, pSBUbi-FRT-Cre-35S/hyg-Hs-FRT-gusA, and pSBUbi-loxP-bar-loxP-FRT-FLP-FRT-gfp (FIG. 2) will be prepared for creeping bentgrass transformation.

To synthesize the Cre-containing construct, pSBUbi-FRT-Cre-35S/hyg-Hs-FRT-gusA, we will first clone the 35S-hyg fragment, released from pSB35S-hyg through HindIII digestion, into the corresponding site of the binary vector, pSBUbi-FRT-hyg-FRT-gusA to replace hyg, producing pSBUbi-FRT-35S/hyg-FRT-gusA. The correct orientation of the inserted 35S-hyg fragment will be verified by restriction digestions and sequencing. The Cre-coding sequence plus nos terminator will then be released by XbaI (flushed by Klenow treatment) and EcoRI digestions from pSBbar-Ubi/Cre, (provided by Dr. Thomas K. Hodges at Purdue University). The Cre-nos fragment will be inserted into the SnaBI-EcoRI sites of pSBUbi-FRT-35S/hyg-FRT-gusA, resulting in pSBUbi-FRT-Cre-35S/hyg-FRT-gusA. The soybean Gmhsp 17.5-E heat-shock promoter, Hs (Ainley and Key, 1990), will be released from pMA406 (provided by Dr. Thomas K. Hodges at Purdue University) by HindIII-SalI digestions, flushed by Klenow treatment and inserted into the blunt-ended NotI site of pSBUbi-FRT-Cre-35S/hyg-FRT-gusA, producing the final construct, pSBUbi-FRT-Cre-35S/hyg-Hs-FRT-gusA. The correct orientation of the heat-shock promoter will be verified by restriction digestions and DNA sequencing.

To synthesize the FLP-containing construct, pSBUbi-loxP-bar-loxP-FRT-FLP-FRT-gfp, the marker gene, bar-coding sequence plus nos terminator will first be released from pSB35S/bar by EcoRI (flushed by Klenow treatment)-BamHI digestions. The released fragment will then be inserted into the SmaI-BamHI sites between the two loxP sites to replace the hyg-nos fragment in pSB35S-lox-hyg-lox/gusA (Hoa et al., 2002), (provided by Dr. Thomas K. Hodges at Purdue University), resulting in pSB35S-lox-bar-lox/gusA. The lox-bar-lox fragment will be released from the pSB35S-lox-bar-lox/gusA vector by SphI (flushed by Klenow treatment)-XbaI digestions and ligated into SmaI-XbaI sites of pSBUbi/gfp resulting in pSBUbi-lox-bar-lox-gfp. Simultaneously, we will also release the FLP-coding sequence plus nos terminator from pBarUbi/FLP by partial EcoRI and complete SmaI digestions. The FLP-nos fragment will then be inserted into the EcoRI-EcoRV sites of p2FRT resulting in pFRT-FLP-FRT. The FRT-FLP-FRT fragment will be released from pFRT-FLP-FRT by SnaBI-StuI digestions and inserted into the SmaI site of pSBUbi-lox-bar-loxgfp, resulting in the final construction, pSBUbi-loxP-bar-loxP-FRT-FLP-FRT-gfp. The correct orientation of FRT-FLP-FRT fragment in the pSBUbi-loxP-bar-loxP-FRT-FLP-FRT-gfp vector will be verified by restriction digestions and sequencing.

The two constructed binary vectors prepared as described above will be introduced into *Agrobacterium tumefaciens* strain, LBA4404 (pSB1) (Komari et al., 1996) by triparental mating or electroporation (Hiei et al., 1994); two methods used routinely for *Agrobacterium* transformation (Luo et al., 2004a; b; 2005; 2006; Longo et al., 2006). The resulting *Agrobacterium* strains will be verified by molecular analysis of plasmid DNA (PCR and Southern analysis) and used for creeping bentgrass transformation via infection of embryogenic callus initiated from mature seeds.

Example 4

Production of Transgenic Turfgrass with a Single-Copy Transgene Insertion of Cre-Containing Construction, pSBUbi-FRT-Cre-35S/hyg-Hs-FRT-gusA, and FLP-Containing Construction, pSBUbi-loxP-bar-loxP-FRT-FLP-FRT-gfp Simultaneously with the vector construction, mature seeds of creeping bentgrass, cv Penn A-4 (Turf-Seed, Inc., Hubbard, Oreg.) will be surface sterilized in 10% (v/v) Clorox® bleach plus two drops of Tween-20™ (Polysorbate 20) with vigorous shaking for 90 min. After rinsing five times in sterile distilled water, the seeds will be placed onto callus-induction medium containing MS basal salts and vitamins (Murashige and Skoog, 1962), 30 g/l sucrose, 500 mg/l casein hydrolysate, 6.6 mg/l 3,6-dichloro-o-anisic acid (dicamba), 0.5 mg/l 6-benzylaminopurine (BAP) and 2 g/l Phytagel. The pH of the medium will be adjusted to 5.7 before autoclaving at 120° C. for 20 min. The culture plates containing prepared seed explants will be kept in the dark at room temperature for 6 weeks. Embryogenic calli will be visually selected and subcultured on fresh callus-induction medium in the dark at room temperature for 1 week before co-cultivation with *Agrobacterium tumefaciens*.

The aforementioned two constructs will be separately introduced into creeping bentgrass (cv Penn A-4) by *Agrobacterium*-mediated transformation using embryogenic callus (Luo et al., 2004a; b; 2005). A reliable transformation system is established that has allowed routine transformation of creeping bentgrass, and several other turf species as well as rice with high efficiency and high frequency of single-copy transgene integration (Luo et al., 2004a; b; 2005; Longo et al., 2006).

The regenerated $T_0$ plants will be transferred into soil and grown in the greenhouse. The plants will be vernalized to ensure that they eventually flower normally so that cross-pollination can be conducted to produce a hybrid in the next step. Molecular characterization of these $T_0$ transformants will be conducted to demonstrate the presence and expression of the introduced foreign genes by PCR, Southern and Northern analyses. The copy number of transgene insertion in transgenic plants also will be determined. When conducting Southern blot analysis on the turf transformants, genomic DNA will be obtained from leaves using the procedure described in the QIAamp Tissue Kit (QIAGEN, Inc., Chatsworth, Calif.). The hyg gene or bar gene will be used as a probe for hybridization following standard molecular biology techniques (Sambrook et al., 1989). Transgenic plants with single-copy transgene insertion will be retained, vernalized and grown in the greenhouse to allow them to flower. Total RNA from leaf tissues of positively identified transgenic plants will be isolated and mRNA accumulation in separate transformants will be determined. The RNeasy Plant Total RNA Kit will be used to simplify RNA isolation procedures (QIAGEN Inc., Chatsworth, Calif.). Ten µg total RNA will be fractionated on agarose gels in denaturing conditions (7.5% formaldehyde) for Northern analysis using the hyg coding sequence or bar coding sequence as a probe for hybridization (Sambrook et al. 1989).

Example 5

Cross-Pollination of Transgenic Plants from the Two Independent Transgenic Lines Harboring Ubi-FRT-Cre-35S/hyg-Hs-FRT-gusA, or Ubi-loxP-bar-loxP-FRT-FLP-FRT-gfp In order to determine whether Cre- and FLP-mediated excisional DNA recombination will remove the unwanted transgenic DNA (coding sequences for selectable markers and the coding sequences for recombinases, Cre and FLP), retaining only the reporter genes or coding sequences, gusA (or in other embodiments, nucleotide sequences, the expression of which results in no or reduced sexual reproduction) and gfp (or in other embodiments, the NOI), the vernalized transgenic plants harboring different gene constructs will be cross-pollinated. Because both the Cre- and FLP-containing $T_0$ plants are hemizygous with respect to transgene insertion, there will be only 25% of the resulting hybrid plants that contain both gene constructs. Those hybrid plants will be identified using PCR analysis to verify the presence of both gusA and gfp coding sequences. These plants will then be grown in the greenhouse and examined for GUS and GFP expression to evaluate the efficiency of Cre- and FLP-mediated excisional DNA recombination and the feasibility of using the dual site-specific DNA recombination systems for the production of environmentally safe, "clean" transgenic plants.

It is also noted that in order to save the time needed for obtaining homozygous transgenic lines through cross-pollination among individuals within a population from a given transgenic event, $T_0$ plants (the hemizygous Cre- and FLP-containing transgenic plants for cross-pollination) can be used to identify, by molecular analysis, those hybrid progeny that inherit both nucleic acid constructs. Simultaneously, cross-pollination will also be conducted among Cre- or FLP-containing individuals originating from the chosen transformation events to eventually achieve homozygous status for the transgenes for future use. Although creeping bentgrass is an outcrossing species with self incompatibility, the individual transgenic $T_0$ plant regenerated from a transformation event can be vegetatively propagated into multiple individuals, leading to a population of transgenic plants with the same genetic background derived from the same transformation event. Cross-pollination among individuals within the population can then be conducted to produce segregating progeny from which transgenic homozygous progeny can be identified. This approach has been successfully demonstrated (Luo et al., 2004a, b; 2005). Using this approach, homozygous transgenic parent lines expressing Cre or FLP can be obtained for use in producing uniform hemizygous hybrid progeny.

It also should be noted that many perennial species, including turfgrass, are improved using "synthetic varieties," i.e., a cultivar may consist of a number of different genotypes. In developing cultivars for commercialization using the methods of the present invention, homozygous transgenic plants from different transformation events representing various genetic backgrounds can be mixed as a synthetic variety for use in the field. This strategy has been used previously in developing glufosinate herbicide-resistant, male-sterile creeping bentgrass cultivar (Luo et al., 2005). Similarly, The *Agrobacterium* CP4 EPSPS (5-enol-pyruvylshikimate-3-phosphate synthase) also has been genetically engineered into creeping bentgrass to create glyphosate (marketed under the trade name Roundup) herbicide-resistant transgenic lines that are currently in the process of applying for the USDA deregulation for Roundup Ready® creeping bentgrass by Scotts and Monsanto (Gardner et al. 2003, 2004; Fei & Nelson, 2004).

Example 6

Evaluation of Efficiencies of Dual Recombination Systems in Catalyzing DNA Recombination, Leading to Environmentally Safe, Clean Transgenic Plants GUS Assay, GFP Expression Analysis by Fluorescence Microscopy, and Molecular Analysis In the hybrid plants harboring both Cre- and FLP-containing gene constructs, the function of recombinase Cre should cause the excision of the loxP-flanked blocking fragment (bar gene), thereby bring into proximity an upstream rice Ubi promoter and a downstream FRT-flanked FLP coding sequence. This will in turn result in FLP expression, and consequently self-excision of the FLP-coding sequence, thus bringing together the upstream rice Ubi promoter and a downstream GFP-coding sequence. Therefore, the removal of FRT-flanked FLP-coding sequence will result in GFP expression. In addition to self-excision of FLP-coding sequence that leads to GFP expression, the expression of recombinase FLP also will cause the excision of the FRT-flanked recombinase Cre-coding sequence as well as its linked marker gene, hyg and the heat-shock promoter (Hs), bringing together the upstream rice Ubi promoter and the downstream reporter gene gusA, resulting in GUS expression. Therefore, GFP and GUS expression as well as molecular analysis will demonstrate the efficiency of the functioning of the dual site-specific recombination system in plants.

The GUS assay, GFP expression and molecular analyses on hybrid plants are conducted as follows:

(1) GUS assay: GUS expression in plants will be assayed by histochemical staining of plant tissues with 1 mM 5-bromo-4-chloro-3-indolyl-β-D-glucuronic acid (X-gluc, Biosynth AG, Staad, Switzerland) as described in Jefferson (1987). Leaves and roots sampled at various developmental stages as well as flowers of the hybrid progeny will be incubated at 37° C. overnight in 100 µl reaction buffer containing X-gluc. Prior to photography, samples will be destained in 70% ethanol.

(2) Fluorescence microscopy of GFP expression: The expression of green fluorescent protein, GFP, in leaves, in roots of various developmental stages as well as in flowers of the hybrid progeny will be visualized with a Zeiss M²BIO Fluorescence Combination Zoom Stereo/Compound microscope. The microscope is equipped with a GFP filter set comprising an exciter filter (BP470/40 nm), a dichromatic beam splitter (495 nm) and a band-pass interference filter (BP 525/50 nm) slider to block the red autofluorescence from chlorophyll. The results will be documented by photograph.

(3) Molecular analyses on the hybrid progeny will be carried out to confirm the DNA excision events. PCR and Southern blot analyses will be conducted to verify Cre- and FLP-mediated DNA recombination in the hybrid progeny in comparison to parental plants. Northern analysis and quantitative RT-PCR will be conducted as well to examine the expression of both gusA gene and gfp gene in the hybrid in comparison to parental controls. We will conduct Northern analysis using procedures described above in Example 4. For conducting quantitative real-time RT-PCR to determine gusA and gfp transcription, five micrograms of purified RNA from leaves, roots and flowers will be treated with 1 unit of RNase-free DNase I (Promega) at 37° C. for 15 min. First-strand cDNA synthesis will be primed with random hexamers (Promega) and catalyzed with Moloney murine leukemia virus (M-MLV) reverse transcriptase (Invitrogen) at 37° C. for 1.5 h. A ten-fold dilution of the reaction products will then be subjected to real-time quantitative RT-PCR, which will be performed on an iCycler iQ (Bio-Rad) using iQ SYBR green Supermix (Bio-Rad) with gene-specific primers 5'-AAAGT-GTACG TATCACCGTTTGTGT-3' (SEQ ID NO:3) and 5'-CAGTAAAGTAGAACGGTTTGTGGTT-3' (SEQ ID NO:4) for gusA gene; 5'-ATGGTGAGCAAGGGCGAGG AGC-3' (SEQ ID NO:5) and 5'-CTTGTACAGCTCGTC-CATGCCG-3' (SEQ ID NO:6) for gfp gene. For each RNA sample, a reaction without reverse transcription will be performed to control for contamination by genomic DNA. The actin gene will be used as an internal control. In the calibration step, a control experiment without cDNA will be performed to test for primer-dimer formation. The PCR program will be approximately as follows: 2 min at 50° C., 10 min at 95° C. for DNA polymerase activation, and 40 cycles of 15 s at 95° C. and 60 s at 60° C. Data collection will be performed at 60° C. The melting curve analysis program will consist of 10 s at 95° C., 30 s at 60° C., and heating to 90° C. at a rate of 0.2° C. s$^{-1}$, data being continuously collected. The data will be analyzed by the $2^{-\Delta\Delta Ct}$ method (Pfaffl, 2001) for relative quantification.

It is noted that low-level recombinase expression may occur in some transgenic plants due to "position effect" of the transgene or nucleic acid inserted in the host genome. This would lead to poor efficacy of Cre- or FLP-mediated recombination, and consequently low level of reporter gene (gusA and gfp) expression. However, Northern analysis to evaluate transgene expression levels in the parental plants as described in Example 4, should allow screening for parental lines having high levels of transgene expression, thereby ensuring high levels of expression of Cre and FLP in the hybrids to achieve efficient DNA recombination.

Example 7

Evaluation of the Efficacy of Soybean Heat-Shock Inducible Promoter in Driving Gene Expression in Heat Shock Treated Cre-Containing Transgenic Plants by GUS Assay As a contingency plan for gene containment, an inducible promoter (e.g., a soybean heat-shock promoter (Hs)) is inserted in front of the gusA gene or coding sequence (total sterility in commercial scenarios) in the Cre-containing construct (FIG. 2). FLP-mediated DNA recombination in the hybrid progeny between Cre- and FLP-expressing parent plants will remove this Hs promoter as well as its linked Cre nucleotide sequence and 35S-driven/hyg nucleotide sequence that are flanked by FRT target sites (FIG. 2). In case of poor recombinase-mediated excisional DNA recombination in the hybrid progeny, heat shock induction will activate the Hs promoter, which will then drive GUS expression (total sterility in commercial scenarios, thus no reproductive growth of transgenics). GUS expression as well as molecular analysis will demonstrate whether the soybean heat-shock promoter functions efficiently in turfgrass in driving induced gene expression. Cre-expressing plants with single-copy transgene insertion and high transgene expression identified in Example 4 will be vegetatively propagated and six individuals for every transformation event will be produced and grown in soil in different pots. After vernalization, three plants from each transformation event will be heat-shocked (4 hours at 37° C.) every day for one week in a growth chamber containing a reservoir of water to maintain humidity. The remaining three plants of each transformation event will be grown under normal conditions in the greenhouse without heat-shock treatment and used as negative controls for GUS expression. Transgenic creeping bentgrass plants constitutively expressing GUS generated previously (Luo et al., 2004b) will be used as positive controls. Leaves and roots sampled one week after heat shock treatments will be subjected to a GUS assay using the same procedure as described above in Example 6 to evaluate the efficacy of induced GUS expression in heat shock-treated Cre-containing transgenics.

Northern analysis will be conducted using procedures described above in Example 4 to verify, at molecular level, the expression levels of the gusA gene or coding sequence in different plants tissues upon heat induction. In addition, following the same procedure described above in Example 6, we will also conduct quantitative real-time RT-PCR using RNA from leaves and roots sampled one week after heat shock treatments to determine gusA transcription.

Heat-shock promoters can function properly in heterologous systems since the response mechanism seems to be evolutionary conserved in many organisms (Wallarath et al., 1994). This has been illustrated by application of the *Drosophila* hsp70 promoter, as well as heat-shock promoters isolated from maize and soybean to control gene expression in heterologous dicot or monocot plant species (Spena et al., 1985; Czarnecka et al., 1989; Ainley and Key, 1990; Rieping and Schoffl, 1992; Kilby et al., 1995; Lyznik et al., 1995 Wang et al., 2005; Cuellar et al., 2006). We anticipated that heat shock activation of this promoter will also lead to GUS expression in transgenic turfgrass (no or reduced reproductive growth of transgenics) and allow evaluating efficacy of this promoter in driving gene expression in turfgrass species. It is noted that alternative inducible gene switch systems relying on other environmental stimuli, or synthetic compounds or developmental and/or cell-specific factors (Zuo et al 2000, 2001; Roslan et al., 2001; Shimizu-Sato et al., 2002; Padidam 2003) also can be employed in the methods described herein for contingency plans for gene containment. Thus, the methods of the present invention of incorporating a contingency plan into the integrated dual site-specific recombination system for gene containment assures that in commercial scenarios, even in the worst cases when efficient site-specific recombination does not occur and the un-desirable DNA can not be removed from transgenic plants due to poor DNA recombination, the induced activation of a total sterility system will inhibit reproductive growth of transgenic plants, therefore preventing transgene escape through pollen and seeds.

Example 8

Preparation of Constructs

Figure 3:
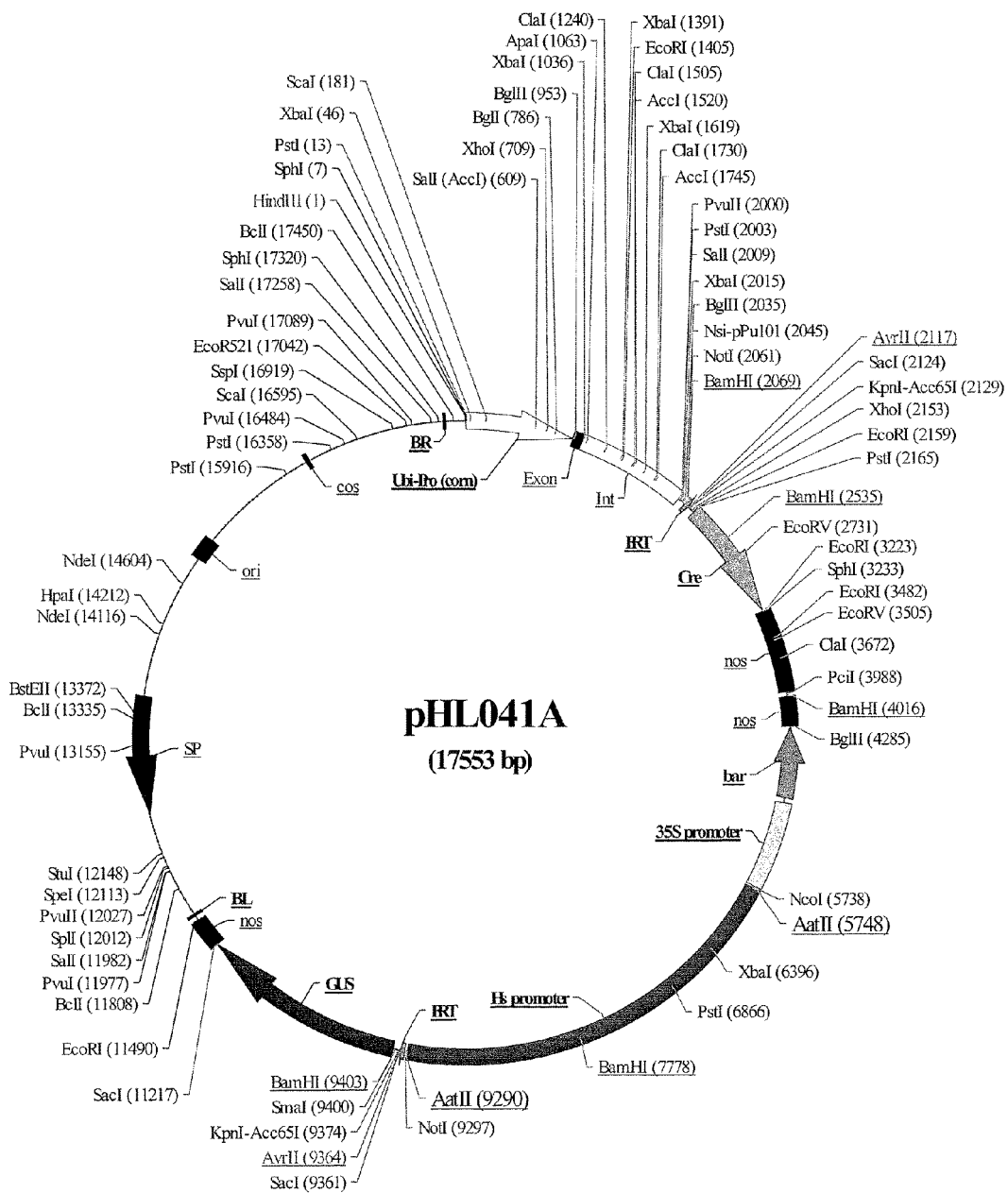
FIG. 3 shows the construct pHL041A.
Figure 4:
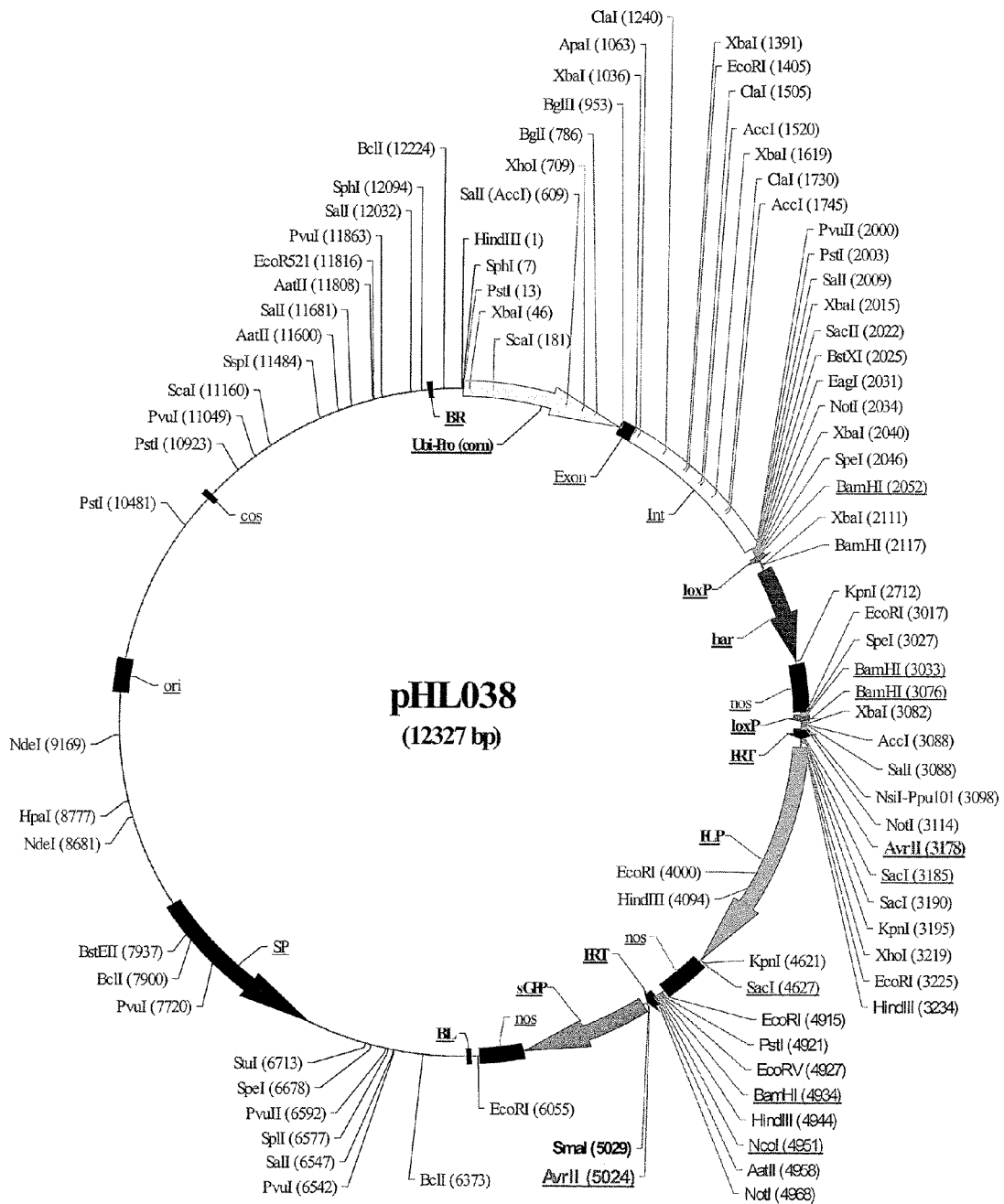
FIG. 4 shows the construct pHL038.

Two constructs, pHL041A and pHL038, were prepared as described above. These constructs are shown in FIGS. 3 and 4, respectively.

Example 9

Genetic Transformation of *Arabidopsis thaliana* and Creeping Bentgrass

The constructs, pHL041A (FIG. 3) and pHL038 (FIG. 4), were each introduced into separate *Agrobacterium tumefaciens*. Using standard techniques known in the art and described above, *Arabidopsis thaliana* and creeping bentgrass plants were then transformed with the constructs, pHL041A and pHL038, via *Agrobacterium*-mediated transformation using the transformed *A. tumefaciens*.

The transgenic lines produced include *A. thaliana* transgenic lines harboring pHL041A, *A. thaliana* transgenic lines harboring pHL038, creeping bentgrass transgenic lines harboring pHL041A and creeping bentgrass transgenic lines harboring pHL038. Transgenic T1 plants of each transgenic line will be examined for transgene integration and expression. Cross-pollination between *A. thaliana* plants harboring pHL041A and pHL038 will be conducted and the hybrid plants will be examined to evaluate the functionality and efficiency of the dual site-specific recombination (i.e., examined for reduced or no sexual reproductive capability and whether unwanted transgenic nucleotide sequences are no longer present). Similarly, creeping bentgrass plants harboring pHL041A and pHL038 will be cross-pollinated and the hybrid plants will be examined for reduced or no sexual reproductive capability and whether unwanted transgenic nucleotide sequences are no longer present.

The foregoing is illustrative of the present invention, and is not to be construed as limiting thereof. The invention is defined by the following claims, with equivalents of the claims to be included therein.

All publications, patent applications, patents and other references cited herein are incorporated by reference in their entireties for the teachings relevant to the sentence and/or paragraph in which the reference is presented.

BIBLIOGRAPHY AND REFERENCES CITED

Ainley W M, Key J L (1990) "Development of a heat shock inducible expression cassette for plants: characterization of parameters for its use in transient expression assays." *Plant Mol Biol* 14:949-967.

Altieri M A (2000) "The ecological impacts of transgenic crops on agroecosystem health." *Ecosystem Health* 6:13-23.

Argos W, Landy A, Abremski K, Egan J D, Haggard-Ljungquist E, Hoess R H, Kalin M L, Kalionis W, Narayama S V L, Pierson L S, Sternberg N, Leong I M (1986) "The integrase family of site-specific recombinases: regional similarities and global diversity." *EMBO J* 5-:433-440.

Austin S, Ziese M, Sternberg N (1981) "A novel role of site-specific recombination in maintenance of bacterial replicons." *Cell* 25:729-736.

Bar M, Leshem B, Gilboa N Gidoni D (1996) "Visual characterization of recombination at FRT-gusA loci in transgenic tobacco mediated by constitutive expression of the native FLP recombinase." *Theor Appl Genet.* 93:407-413.

Bayley C C, Morgan M, Dale E C, Ow D W (1992) "Exchange of gene activity in transgenic plants catalyzed by the Cre-lox site-specific recombination system." *Plant Mol Biol* 18:353-361.

Broach J R, Guarascio V R, Jayaram M (1982) "Recombination within the yeast plasmid 2 micron circle is site-specific." *Cell* 29:227-234.

Chou T B, Perrimon N (1992) "Use of a yeast site-specific recombinase to produce female germline chimeras in *Drosophila*." *Genetics* 131:643-653.

Coen E S, Romero J M, Doyle S, Elliott R, Murphy G, Carpenter R (1990) "Floricaula: a homeotic gene required for flower development in *Antirrhinum majus*." *Cell* 63:1311-1322.

Craig N L (1988) "The mechanism of conservative site-specific recombination." *Annu Rev Genet.* 22:77-105.

Cox M M (1983) "The FLP protein of the yeast 2 μm plasmid: expression of a eukaryotic genetic recombination system in *E. coli*." *Proc Natl Acad Sci USA* 80:4223-4227.

Cuellar, W, Gaudin A, Dennis Solórzano D, Casas A, Nopo L, Chudalayandi P, Medrano G, Kreuze J, Ghislain M (2006) "Self-excision of the antibiotic resistance gene nptII using a heat inducible Cre-loxP system from transgenic potato." *Plant Mol Biol* 62:71-82.

Czarnecka E, Key J L, Gurley W B (1989) "Regulatory domains of the Gmhsp 17.5-E heat shock promoter of soybean." *Mol Cell Biol* 9:3457-3463.

Dale E C, Ow D W (1990) "Intra- and intermolecular site-specific recombination in plant cells mediated by bacteriophage P1 recombinase." *Gene* 91:79-85.

Dale E C, Ow D W (1991) "Gene transfer with subsequent removal of the selection gene from the host genome." *Proc Natl Acad Sci USA* 88:10558-10562.

Dale P J (1992) "Spread of engineered genes to wild relatives." *Plant Physiol.* 100: 13-15.

Dale P J (1993) "The release of transgenic plants into agriculture." *J Agr Sci* 120:1-5.

Dale P J, Clarke B, Fontes E M G (2002) "Potential for the environmental impact of transgenic crops." *Nat. Biotechnol.* 20:567-574.

Daniell H (2002) "Molecular strategies for gene containment in transgenic crops." *Nat. Biotechnol.* 20:581-586.

Eastham K, Sweet J (2002) "Genetically modified organisms (GMOs): the significance of gene flow through pollen transfer." European Environment Agency, Denmark.

Ellstrand N C, Hoffman C A (1990): Hybridization as an avenue of escape for engineered genes." *Bioscience* 40:438-442.

Ellstrand N C, Prentice H C, Hancock J F. (1999). "Gene flow and introgression from domesticated plants into their wild relatives." *Annu. Rev. Ecol. Syst.* 30:539-563.

Fei S, Nelson E (2004) "Greenhouse evaluation of fitness-related reproductive traits in Roundup®-tolerant transgenic creeping bentgrass (*Agrostis stolonifera* L.)". *In Vitro Cell. Dev. Biol. Plant* 40:266-273.

Gardner D S, Danneberger T K, Nelson E K (2004) "Lateral spread of glyphosate-resistant transgenic creeping bentgrass (*Agrostis stolonifera*) lines in established turfgrass swards." *Weed Technol* 18:773-778.

Gardner D S, Daimeberger T K, Nelson E, Meyer W, Plumley K (2003) "Relative fitness of glyphosate-resistant creeping bentgrass lines in Kentucky bluegrass." *Hort Science* 38:455-459.

Golic K G, Lindquist S (1989) "The FLP recombinase of yeast catalyzes site-specific recombination in the *Drosophila* genome." *Cell* 59:499-509.

Hiei Y, Ohta S, Komari T, Kumashiro T (1994) "Efficient transformation of rice (*Oryza sativa* L.) mediated by *Agrobacterium* and sequence analysis of the boundaries of the T-DNA." *Plant J* 6:271-282.

Hoa T T C, Bong B B, Huq E, Hodges T K (2002) "Cre/lox site-specific recombination controls the excision of a transgene from the rice genome." *Theor Appl Genet.* 104:518-525.

Hoess R H, Ziese M, Sternberg N (1982) "P1 site-specific recombination: nucleotide sequence of the recombining sites." *Proc Natl Acad Sci USA* 79:3398-3402.

Hoffman C A (1990) "Ecological risks of genetic engineering of crop plants." *Bio Science* 40:434-437.

Hu Q, Nelson K, Luo H (2006) "FLP-mediated site-specific recombination for genome modification in turfgrass." *Biotechnol Lett* 28:1793-1804.

Hu Q, Nelson K, Viola D, Zeng P, Lickwar C, Chandlee J M, Kausch A P, Luo H (2007) "FLP-mediated recombination for use in hybrid rice production." *Nature Biotechnology* (submitted).

Huang L C, Wood E A, Cox M M (1991) "A bacterial model system for chromosomal targeting." *Nucl Acids Res* 19:443-448.

Jayaram M (1985) "Two-micrometer circle site-specific recombination: The minimal substrate and the possible role of flanking sequences." *Proc Natl Acad Sci USA* 82:5875-5879.

Jefferson R A (1987) "Assaying chimeric genes in plants: The GUS gene fusion system." *Plant Mol Biol Rep* 5:387-405.

Kilby N J, Davies G J, Snaith M R, Murray A H (1995) "FLP recombinase in transgenic plants: constitutive activity in stably transformed tobacco and generation of marked cell clones in *Arabidopsis*." *Plant J* 8:637-652.

Komari T, Hiei Y, Saito Y, Murai N, Kumashiro T (1996) "Vectors carrying two separate T-DNAs for co-transformation of higher plants mediated by *Agrobacterium tumefaciens* and segregation of transformants free from selection markers." *Plant J* 10: 165-174.

Kyozuka J, Konishi S, Nemoto K, Izawa T, Shimamoto K (1998) "Down-regulation of RFL, the FLO/LFY homolog of rice, accompanied with panicle branch initiation." *Proc Natl Acad Sci USA* 95:1979-1982.

Lloyd A M, Davis R W (1994) "Functional expression of the yeast FLP/FRT site-specific recombination system in *Nicotiana tabacum*." *Mol Gen Genet.* 242:653-657.

Longo C, Lickwar C, Hu Q, Nelson K, Viola D, Hague J, Chandlee J M, Luo H and Kausch A P (2006) "*Agrobacterium tumefaciens*-mediated transformation of turfgrasses." In: *Methods in Molecular Biology*, Vol 44, Wang K (ed.), Humana Press Inc., Totowa, N.J. (in press).

Luo H, Hu Q, Nelson K, Longo C, Kausch A P (2004a) "Controlling transgene escape in genetically modified grasses." In: *Molecular Breeding of Forage and Turf*, Hopkins A, Wang Z Y, Mian R, Sledge M and Barker R (eds.), Kluwer Academic Publishers, Dordrecht/Boston/London, p 245-254.

Luo H, Hu Q, Nelson K, Longo C, Kausch A P, Chandlee J M, Wipff J K, Fricker C R (2004b) "*Agrobacterium tumefaciens*-mediated creeping bentgrass (*Agrostis stolonifera* L.) transformation using phosphinothricin selection results in a high frequency of single-copy transgene integration." *Plant Cell Rep* 22:645-652.

Luo H, Kausch A P, Hu Q, Nelson K, Wipff J K, Crystal C R, Owen T P, Moreno M A, Lee J-Y, Hodges T K (2005) "Controlling transgene escape in GM creeping bentgrass." *Mol Breed* 16:185-188.

Luo H, Kausch A P (2002) "Application of FLP/FRT site-specific DNA recombination system in plants." In: *Genetic Engineering, Principles and Methods*, Vol 24 (Jane K. setlow ed). Kluwer Academic/Pleum Publishers, New York, N.Y., p. 1-16.

Luo H, Lyznik L A, Gidoni, Hodges T K (2000) "FLP-mediated recombination for use in hybrid plant production." *Plant J* 23:423-430.

Lyznik L A and Hodges T K (1996) "FLP-mediated recombination of FRT sites in the maize genome." *Nucleic Acids Res* 24:3784-3789.

Lyznik L A, Hirayama L, Rao K A, Abad A and Hodges T K (1995) "Heat-inducible expression of FLP gene in maize cells." *Plant J* 8:177-186.

Lyznik L A, Mitchell J C, Hirayama L, Hodges T K (1993) "Activity of yeast FLP recombinase in maize and rice protoplasts." *Nucleic Acids Res* 21:969-975.

Marvier M, Van Acker R C (2005) "Can crop transgenes be kept on a leash?" *Front Ecol Environ.* 3:99-106.

Murashige, Skoog F (1962) "A revised medium for rapid growth and bioassays with tobacco tissue cultures." *Physiol Plant* 15:473-497.

Odell J, Caimi P, Sauer B, Russell S (1990) "Site-directed recombination in the genome of transgenic tobacco." *Mol Gen Genet* 223:369-378.

Odell, J T, Russell, S H (1994) "Use of site-specific recombination systems in plants." In: *Homologous recombination in plants*, edited by Paszkowski, J. Dordrecht: Kluwer Academic Publishers, p. 219-270.

O'Gorman S, Fox D T, Wahl G M (1991) "Recombinase-mediated gene activation and site-specific integration in mammalian cells." *Science* 251:1351-1355.

Osborne B I, Wirtz U, Baker B (1995) "A system for insertional mutagenesis and chromosomal rearrangement using the Ds transposon and Cre-lox." *Plant J* 7:687-701.

Ow D W, Medberry S L (1995) "Genome manipulation through site-specific recombination." *Crit Rev Plant Sci* 14:239-261.

Padidam M (2003) "Chemically regulated gene expression in plants." *Curr Opin Plant Biol* 6:169-177.

Pfaffl M W (2001) "A new mathematical model for relative quantification in real-time RT-PCR." *Nucleic Acids Res* 29:e45.

Pilson D, Prendeville H R (2004) "Ecological effects of transgenic crops and the escape of transgenes into wild populations." *Annu Rev of Ecol, Evol S* 35:149-174.

Qin M, Bayley C, Stockton T, Ow D W (1994) "Cre recombinase-mediated site-specific recombination between plant chromosomes." *Proc Natl Acad Sci USA* 91:1706-1710.

Reichman J R, Watrud L S, Lee E H, Burdick C A, Bollman M A, Stonn M J, King G A, Mallory-Smith C (2006) "Establishment of transgenic herbicide-resistant creeping bentgrass (*Agrostis stolonifera* L.) in nonagronomic habitats." *Mol Ecol* 15:4243-4255.

Rieping M, Schoffl F (1992) "Synergistic effect of upstream sequences, CCAAT box elements, and HSE sequences for enhanced expression of chimaeric heat shock genes in transgenic tobacco." *Mol Gen Genet* 231:226-232.

Rogers H J, Parkes H C (1995) "Transgenic plants and the environment." *J. Exp. Bot.* 46:467-488.

Rong Y S, Golic K G (2000) "Gene targeting by homologous recombination in *Drosophila.*" *Science* 288:2013-8.

Roslan H A, Salter M G, Wood C D, White M R H, Croft K P, Robson F, Coupland G, Doonan J, LaufS P, Tomsett A B, Caddick M X (2001) "Characterization of the ethanol-inducible alc gene expression system in *Arabidopsis thaliana.*" *Plant J* 28:225-235.

Sadowski P D (1995) "The Flp recombinase of the 2-μmplasmid of *Saccharomyces cerevisiae.*" *Prog Nucleic Acids Re* 51:53-91.

Sambrook J, Fritsch E F, Maniatis T (1989) "Molecular Cloning: A Laboratory Manual." Cold Spring Harbor, N.Y.: Cold Spring Harbor Laboratory Press.

Shimizu-Sato S, Huq E, Tepperman J M, Quail P (2002) "A light-switchable gene promoter system." *Nat Biotechnol* 20:1041-1044.

Sonti R V, Tisser A-F, Wong D, Viret J F, Signer E R (1995) "Activity of the yeast FLP recombinase in *Arabidopsis.*" *Plant Mol Biol* 28:1127-1132.

Spena A, Haun R, Ziervogel U, Saedler H, Schell J (1985) "Construction of a heat-inducible gene for plants: demonstration of a heat-inducible activity of the *Drosophila* hsp70 promoter in plants." *EMBO J* 4:2739-2743.

Sreekala C, Wu L, Gu K, Wang D, Tian D, Yin Z (2005) "Excision of a selectable marker in transgenic rice (*Oryza sativa* L.) using a chemically regulated Cre/loxP system." *Plant Cell Rep* 24:86-94.

Srivastava V, Anderson O D, Ow D W (1999) "Single-copy transgenic wheat generated through the resolution of complex integration patterns." *Proc Natl Acad Sci USA* 96:11117-11121.

Srivastava V, Ow D W (2001) "Biolistic mediated site-specific integration in rice." *Mol Breeding* 8:345-350.

Stewart C N Jr, Halfhill M D, Warwick S I (2003) "Transgene introgression from genetically modified crops to their wild relatives." *Nat Rev Genet.* 4:806-817.

Stuurman J, de Vroomen M J, Nijkamp H J J, van Haaren M J J (1996) "Single-site manipulation of tomato chromosomes in vitro and in vivo using Cre-lox site-specific recombination." *Plant Mol Biol* 32:901-913.

Toriyama K, Chiba A, Nakagawa Y (2003) "Visualization of somatic deletions mediated by R/RS site-specific recombination and induction of germinal deletions caused by callus differentiation and regeneration in rice." *Plant Cell Rep* 21:605-610.

Wang Y, Chen B, Hu Y, Li J, Lin Z (2005) "Inducible excision of selectable marker gene from transgenic plants by the Cre/lox site-specific recombination system." *Transgenic Res* 14:605-614.

Watrud L S, Lee E H, Fairbrother A, Burdick C, Reichman J R, Bollman M, Storm M, King G, Van de Water P K (2004) "Evidence for landscape-level, pollen-mediated gene flow from genetically modified creeping bentgrass with CP4 EPSPS as a marker." *Proc. Nat. Acad. Sci. USA* 101:14533-14538.

Weigel D, Alvarez J, Smyth D R, Yanofsky M F, Meyerowitz E M (1992) "LEAFY controls floral meristem identity in *Arabidopsis.*" *Cell* 69:843-859.

Wipff J K, Fricker C (2000) "Determining gene flow of transgenic creeping bentgrass and gene transfer to other bentgrass species." *Diversity* 16:36-39.

Zhang Y, Li H, Ouyang B, Lu Y, Ye Z (2006) "Chemical-induced autoexcision of selectable markers in elite tomato plants transformed with a gene conferring resistance to lepidopteran insects." *Biotechnol Lett* DOI 10.1007/s10529-006-9081-z.

Zuo J, Niu Q W, Chua N H (2000) "An estrogen receptor-based transactivator XVE mediates highly inducible gene expression in transgenic plants." *Plant J* 24:265-273.

Zuo J. Niu Q W, Moller S G, Chua N H (2001) "Chemical-regulated, site-specific DNA excision in transgenic plants." *Nat Biotechnol* 19:157-161.

That which is claimed is:

1. A method of producing a transgenic hybrid plant having no or reduced sexual reproduction, the method comprising:
   (a) stably transforming a first plant with a first nucleic acid construct comprising:
      (i) a promoter, P1;
      (ii) a site specific recombinase, RS1;
      (iii) a promoter, P2;
      (iv) a selectable marker, SM1;
      (v) a promoter P3;
      (vi) at least one nucleotide sequence the expression of which results in no or reduced sexual reproduction, NRSR; and
      (vii) at least two target sites, TRS2, specific for a site specific recombinase, RS2 that is different from the site specific recombinase, RS1,
      and further wherein P1 is operably located upstream of RS1, P2 is operably located upstream of SM1 and downstream of RS1, P3 is operably located upstream of NRSR and downstream of SM1, a first TRS2 is located immediately downstream of P1 and a second TRS2 is located upstream of NRSR and downstream of P3;
   (b) stably transforming a second plant with a second nucleic acid construct comprising:
      (i) a promoter, P4;
      (ii) a site specific recombinase, RS2, that is different from the site specific recombinase, RS1, of (a);
      (iii) a selectable marker, SM2;
      (iv) at least one nucleotide sequence of interest, NOI;
      (v) at least two target sites, TRS1, specific for the site specific recombinase, RS1; and
      (vi) at least two target sites, TRS2, specific for the site specific recombinase, RS2,
      and further wherein P4 is operably located upstream of SM2, RS2 is located downstream of SM2, a first TRS1 is located immediately downstream of P4, a second TRS1 is located immediately downstream of SM2, a first TRS2 is located immediately upstream of RS2 and downstream of the second TRS1, a second TRS2 is located immediately downstream of RS2 and the NOI is located immediately downstream of the second TRS2; and
   (c) cross-pollinating the stably transformed first plant of (a) with the stably transformed second plant of (b) to produce a transgenic hybrid plant having no or reduced sexual reproduction.

2. The method of claim 1, wherein the promoter, P1, is a ubiquitin promoter.

3. The method of claim 1, wherein the promoter, P2, is a 35S promoter.

4. The method of claim 1, wherein the site specific recombinase, RS1, and the target site for the site specific recombinase, TRS1, are selected from the group of recombinase/target sites consisting of FLP/FRT, Cre/lox, R/RS and Gin/gix.

5. The method of claim 1, wherein the site specific recombinase, RS2, and the target site for the site specific recombinase, TRS2, are selected from the group of recombinase/target sites consisting of FLP/FRT, Cre/lox, R/RS and Gin/gix.

6. The method of claim 1, wherein the selectable marker, SM1, and the selectable marker, SM2, are selected from the group consisting of a nucleotide sequence encoding a product that confers antibiotic resistance, a nucleotide sequence encoding a product that confers herbicide resistance or tolerance, a nucleotide sequence encoding a fluorescing protein, a nucleotide sequence encoding an enzyme, a nucleotide sequence the expression of which results in a nutritional deficiency, and any combination thereof.

7. The method of claim 6, wherein the nucleotide sequence encoding a product that confers antibiotic resistance is selected from the group consisting of hyg, neo, tet, ble, kan, pur, amp, aadA, and any combination thereof.

8. The method of claim 6, wherein the nucleotide sequence encoding a product that confers herbicide resistance or tolerance is selected from the group consisting of nucleotide sequences encoding products that confer resistance or tolerance to the herbicides bialaphos, glyphosate, sulfonylurea, glufosinate ammonium, bromoxynil, 2,4-dichlorophenoxyacetate, and any combination thereof.

9. The method of claim 6, wherein the selectable marker, SM1, is hyg.

10. The method of claim 6, wherein the second selectable marker, SM2, is bar.

11. The method of claim 6, wherein the nucleotide sequence encoding a fluorescing protein is selected from the group consisting of a nucleotide sequence that encodes green fluorescent protein, a nucleotide sequence that encodes luciferase, a nucleotide sequence that encodes red fluorescent protein, and any combination thereof.

12. The method of claim 6, wherein the nucleotide sequence encoding a hydrolyzing enzyme is selected from the group consisting of a nucleotide sequence encoding β-galactosidase, a nucleotide sequence encoding β-glucuronidase, and any combination thereof.

13. The method of claim 6, wherein the nucleotide sequence the expression of which results in a nutritional deficiency is selected from the group consisting of a nucleotide sequence the expression of which results in a plant having a uracil deficiency, a nucleotide sequence the expression of which results in a plant having a histidine deficiency, a nucleotide sequence the expression of which results in a plant having a leucine deficiency, and any combination thereof.

14. The method of claim 1, wherein the promoter, P3, is a heat shock promoter.

15. The method of claim 1, wherein the nucleotide sequence the expression of which results in no or reduced sexual reproduction, NRSR, is selected from the group consisting of barnase, an RNAi or antisense of a pollen- and tapetum-specific nucleotide sequence, an RNAi of a FLORICAULA/LEAFY nucleotide sequence and an antisense of a FLORICAULA/LEAFY nucleotide sequence, and any combination thereof.

16. The method of claim 1, wherein the promoter, P4, is a ubiquitin promoter.

17. The method of claim 1, wherein the nucleotide sequence of interest, NOI, is a nucleotide sequence the expression of which results in a phenotype selected from the group consisting of herbicide resistance, drought tolerance, salt tolerance, cold tolerance, pigmentation, increased root growth, increased vegetative growth, enhanced seed production, enhanced phosphate uptake, phytoremediation, disease resistance, insect resistance, wear tolerance (high traffic tolerance), early flowering, shade tolerance, hypoxia tolerance, fungal resistance, stay-green, delayed senescence, decreased nitrogen, endophyte-enhanced, and any combination thereof.

18. The method of claim 1, wherein the first plant and the second plant are selected from the group consisting of angiosperms, gymnosperms, bryophytes, ferns and fern allies.

19. The method of claim 18, wherein the first plant and the second plant are angiosperms.

20. The method of claim 19, wherein the first plant and the second plant are dicots.

21. The method of claim 19, wherein the first plant and the second plant are monocots.

22. The method of claim 21, wherein the monocot is a turfgrass.

23. The method of claim 1, wherein stably transforming a plant comprises introducing a nucleic acid construct into a plant or plant cell by a transformation method selected from the group consisting of bacterial-mediated nucleic acid delivery, viral-mediated nucleic acid delivery, microinjection, infiltration, microparticle bombardment, electroporation, sonication, PEG-mediated nucleic acid uptake, and any combination thereof.

24. A transgenic hybrid plant made by the method of claim 1.

25. A transgenic hybrid plant comprising:
(a) a first nucleic acid construct comprising:
  (i) a promoter, P1;
  (ii) a target site, TRS2, specific for a site specific recombinase, RS2; and
  (iii) at least one nucleotide sequence the expression of which results in no or reduced sexual reproduction, NRSR, and wherein P1 is upstream of and operably associated with NRSR, and the target site, TRS2, is immediately downstream of P1; and
(b) a second nucleic acid construct comprising:
  (i) a promoter, P4;
  (ii) a target site, TRS2 specific for the site specific recombinase, RS2;
  (iii) a target site, TRS1, specific for a site specific recombinase, RS1; and
  (iv) at least one nucleotide sequence of interest, NOI, and wherein P4 is upstream of and operably associated with the NOI, and the target site, TRS1, is immediately downstream of P4 and the NOI is immediately downstream of TRS2.

26. A method of reducing transgene flow to non-transgenic plants, comprising planting a field with a plurality of plants comprising the plant of claim 24.

27. A method of reducing transgene flow to non-transgenic plants, comprising planting a field with a plurality of plants comprising the plant of claim 25.

28. A nucleic acid construct comprising:
(a) a promoter, P1;
(b) a site specific recombinase, RS1;
(c) a promoter, P2;
(d) a selectable marker, SM1;
(e) a promoter P3;
(f) at least one nucleotide sequence the expression of which results in no or reduced sexual reproduction, NRSR; and
(g) at least two target sites, TRS2, specific for a site specific recombinase, RS2, wherein RS2 is different from the site specific recombinase, RS1, of (b) above, and
further wherein P1 is located upstream of and operably associated with RS1, P2 is located downstream of RS1 and upstream of and operably associated with SM1, P3 is located downstream of SM1 and upstream of and operably associated with NRSR, a first TRS2 is located immediately downstream of P1 and a second TRS2 is located upstream of NRSR and downstream of P3.

29. A nucleic acid construct comprising:
(a) a promoter, P4;
(b) a selectable marker, SM2;
(c) a site specific recombinase, RS2;
(d) at least two target sites, TRS2, specific for the site specific recombinase, RS2;
(e) at least two target sites, TRS1, specific for a site specific recombinase, RS1 that is different from the site specific recombinase RS2 of (c) above; and
(f) at least one nucleotide sequence of interest, NOI; and
further wherein P4 is located upstream of and operably associated with SM2, RS2 is located downstream of SM2, a first TRS1 is located immediately downstream of P4, a second TRS1 is located immediately downstream of SM2, a first TRS2 is located immediately upstream of RS2 and downstream of the second TRS1, a second TRS2 is located immediately downstream of RS2 and the NOI is located immediately downstream of the second TRS2.

30. A transgenic plant comprising the nucleic acid construct of claim 28.

31. A transgenic plant comprising the nucleic acid construct of claim 29.

32. A transgenic pollen grain of the transgenic plant of claim 30.

33. A transgenic pollen grain of the transgenic plant of claim 31.

34. A transgenic ovule of the transgenic plant of claim 30.

35. An transgenic ovule of the transgenic plant of claim 31.

36. A tissue culture of regenerable transgenic cells of the transgenic plant of claim 30.

37. A tissue culture of regenerable transgenic cells of the transgenic plant of claim 31.

38. A transgenic seed of the transgenic plant of claim 30, wherein the transgenic seed comprises the nucleic acid construct.

39. A transgenic seed of the transgenic plant of claim 31, wherein the transgenic seed comprises the nucleic acid construct.

* * * * *

UNITED STATES PATENT AND TRADEMARK OFFICE
CERTIFICATE OF CORRECTION

PATENT NO. : 8,237,015 B2  
APPLICATION NO. : 12/174066  
DATED : August 7, 2012  
INVENTOR(S) : Luo Page 1 of 1

It is certified that error appears in the above-identified patent and that said Letters Patent is hereby corrected as shown below:

In the Patent:

Column 3, Line 40: Please correct "O'Gonnan et al., 1991;"
to read -- O'Gorman et al., 1991; --

Column 19, Line 4: Please correct "amp or, aada gene"
to read -- amp or, aadA gene --

Column 25, Line 17: Please correct "described by 1uchi et al."
to read -- described by Iuchi et al. --

Signed and Sealed this
Fifth Day of February, 2013

Teresa Stanek Rea
*Acting Director of the United States Patent and Trademark Office*

SEQUENCE LISTING

<160> NUMBER OF SEQ ID NOS: 6

<210> SEQ ID NO 1
<211> LENGTH: 34
<212> TYPE: DNA
<213> ORGANISM: Bacteriophage lambda

<400> SEQUENCE: 1
gaagttccta tactttctag agaataggaa cttc                              34

<210> SEQ ID NO 2
<211> LENGTH: 34
<212> TYPE: DNA
<213> ORGANISM: Bacteriophage lambda

<400> SEQUENCE: 2
ataacttcgt ataatgtatg ctatacgaag ttat                              34

<210> SEQ ID NO 3
<211> LENGTH: 25
<212> TYPE: DNA
<213> ORGANISM: Artificial
<220> FEATURE:
<223> OTHER INFORMATION: RT-PCR primer

<400> SEQUENCE: 3
aaagtgtacg tatcaccgtt tgtgt                                        25

<210> SEQ ID NO 4
<211> LENGTH: 25
<212> TYPE: DNA
<213> ORGANISM: Artificial
<220> FEATURE:
<223> OTHER INFORMATION: RT-PCR primer

<400> SEQUENCE: 4
cagtaaagta gaacggtttg tggtt                                        25

<210> SEQ ID NO 5
<211> LENGTH: 22
<212> TYPE: DNA
<213> ORGANISM: Artificial
<220> FEATURE:
<223> OTHER INFORMATION: RT-PCR primer

<400> SEQUENCE: 5
atggtgagca agggcgagga gc                                           22

<210> SEQ ID NO 6
<211> LENGTH: 22
<212> TYPE: DNA
<213> ORGANISM: Artificial
<220> FEATURE:
<223> OTHER INFORMATION: RT-PCR primer

<400> SEQUENCE: 6
cttgtacagc tcgtccatgc cg                                           22